(12) United States Patent  (10) Patent No.: US 7,621,026 B2
Lindsay et al.  (45) Date of Patent: Nov. 24, 2009

(54) ACTIVATABLE FASTENING SYSTEM AND WEB HAVING ELEVATED REGIONS AND FUNCTIONAL MATERIAL MEMBERS

(75) Inventors: Jeffrey Dean Lindsay, Appleton, WI (US); Fung Jou-Chen, Appleton, WI (US); Thomas Harold Roessler, Appleton, WI (US); Daniel Lee Ellingson, Appleton, WI (US); Walter Caswell Reade, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/942,801

(22) Filed: Nov. 20, 2007

(65) Prior Publication Data

US 2008/0081147 A1  Apr. 3, 2008

Related U.S. Application Data

(62) Division of application No. 10/743,556, filed on Dec. 22, 2003, now Pat. No. 7,331,087.

(51) Int. Cl.
*A44B 18/00*  (2006.01)
(52) U.S. Cl. .......................................... 24/442; 24/450
(58) Field of Classification Search ............... 24/442, 24/306, 450–452; 428/100; 604/391
See application file for complete search history.

(56) References Cited

U.S. PATENT DOCUMENTS

| 2,029,951 A | 2/1936 | Smith |
| 3,093,600 A | 6/1963 | Spencer et al. |
| 3,134,152 A | 5/1964 | Pei |
| 3,522,196 A | 7/1970 | Dorier et al. |
| 3,537,123 A | 11/1970 | Leland |
| 3,886,617 A | 6/1975 | Labran et al. |
| 4,018,575 A | 4/1977 | Davis et al. |
| 4,125,664 A | 11/1978 | Giesemann |
| 4,188,447 A | 2/1980 | Ehlenz |
| 4,225,997 A | 10/1980 | Thomas et al. |
| 4,254,527 A | 3/1981 | Pfeifer |

(Continued)

FOREIGN PATENT DOCUMENTS

CH  360592  2/1962

(Continued)

OTHER PUBLICATIONS

Abstract of EP 0017671 published Oct. 29, 1980.

(Continued)

*Primary Examiner*—James R Brittain
(74) *Attorney, Agent, or Firm*—Dority & Manning, P.A.

(57) ABSTRACT

A web for use in applying a functional material is provided. The web includes a layer that has a plurality of elevated regions. The layer defines a plurality of cavities such that the cavities are located between adjacent elevated regions. A plurality of depressed regions are located on the layer intermediate the elevated regions. The layer has a longitudinal direction and a longitudinal mid-plane defined therethrough. A plurality of functional material members are located in the cavities of the layer. The functional material members are adapted for adhesion of particles or surfaces thereon. The layer is extendable in the longitudinal direction so that the elevated regions are moved in a direction towards the longitudinal mid-plane.

10 Claims, 19 Drawing Sheets

U.S. PATENT DOCUMENTS

| | | | |
|---|---|---|---|
| 4,334,971 | A | 6/1982 | Mahnke et al. |
| 4,517,703 | A | 5/1985 | Koke |
| 4,666,948 | A | 5/1987 | Woerner et al. |
| 4,794,028 | A | 12/1988 | Fischer |
| 4,870,725 | A | 10/1989 | Dubowik |
| 4,965,122 | A | 10/1990 | Morman |
| 4,981,747 | A | 1/1991 | Morman |
| 5,190,985 | A | 3/1993 | Mader |
| 5,226,922 | A | 7/1993 | Mori |
| 5,234,969 | A | 8/1993 | Clark et al. |
| 5,260,015 | A | 11/1993 | Kennedy et al. |
| 5,336,545 | A | 8/1994 | Morman |
| 5,413,853 | A | 5/1995 | Imashiro et al. |
| 5,600,865 | A | 2/1997 | Morrison |
| 5,624,427 | A | 4/1997 | Bergman et al. |
| 5,779,691 | A | 7/1998 | Schmitt |
| 6,021,542 | A | 2/2000 | Norman |
| 6,112,362 | A | 9/2000 | Parko et al. |
| 6,123,695 | A | 9/2000 | Skog et al. |
| 6,133,332 | A | 10/2000 | Ide et al. |
| 6,142,986 | A | 11/2000 | Lord et al. |
| 6,393,673 | B1 | 5/2002 | Kourtidis et al. |
| 6,402,731 | B1 | 6/2002 | Surprise et al. |
| 6,436,234 | B1 | 8/2002 | Chen et al. |
| 6,503,615 | B1 | 1/2003 | Horii et al. |
| 6,608,118 | B2 | 8/2003 | Kosaka et al. |
| 6,617,490 | B1 | 9/2003 | Chen et al. |
| 6,737,160 | B1 | 5/2004 | Full et al. |
| 7,140,081 | B2 * | 11/2006 | Browne et al. .............. 24/442 |
| 7,200,902 | B2 * | 4/2007 | Browne et al. .............. 24/442 |
| 2002/0169435 | A1 | 11/2002 | Neeb et al. |
| 2003/0044569 | A1 | 3/2003 | Kacher et al. |
| 2003/0124312 | A1 | 7/2003 | Autumn |
| 2003/0135181 | A1 | 7/2003 | Chen et al. |
| 2003/0164175 | A1 | 9/2003 | Linzell |
| 2003/0208888 | A1 | 11/2003 | Fearing et al. |
| 2004/0086320 | A1 | 5/2004 | Policicchio et al. |
| 2004/0111817 | A1 | 6/2004 | Chen et al. |
| 2004/0115431 | A1 | 6/2004 | Chen et al. |
| 2005/0132518 | A1 | 6/2005 | Chen et al. |
| 2005/0132519 | A1 | 6/2005 | Chen et al. |

FOREIGN PATENT DOCUMENTS

| | | |
|---|---|---|
| DE | 2643717 | 8/1977 |
| DE | 8511694 | 11/1994 |
| DE | 29813214 | 10/1998 |
| EP | 0011055 | 5/1980 |
| EP | 0017671 | 10/1980 |
| EP | 0370697 | 5/1990 |
| EP | 0856276 | 8/1998 |
| EP | 1314390 | 5/2003 |
| FR | 1195436 | 11/1959 |
| FR | 2840523 | 12/2003 |
| GB | 664694 | 1/1952 |
| GB | 1131846 | 10/1968 |
| GB | 1354576 | 6/1974 |
| GB | 1443024 | 7/1976 |
| GB | 2125689 | 3/1984 |
| WO | WO 9842819 | 1/1998 |
| WO | WO 0000148 | 1/2000 |
| WO | WO 0111004 | 2/2001 |
| WO | WO 0141622 | 6/2001 |
| WO | WO 0149776 | 7/2001 |
| WO | WO 0154552 | 8/2001 |
| WO | WO 0200088 | 1/2002 |
| WO | WO 03001962 | 1/2003 |
| WO | WO 03004748 | 1/2003 |

OTHER PUBLICATIONS

Abstract of EP 0856276 published Aug. 5, 1998.

Abstract of FR2840523 published Dec. 12, 2003.

Autumn et al. "Evidence for van der Waals Adhesion in Gecko Setae", Proceeding of the National Academy of Sciences of the United States of America, vol. 99, No. 19, pp. 12,252-12,256.

* cited by examiner

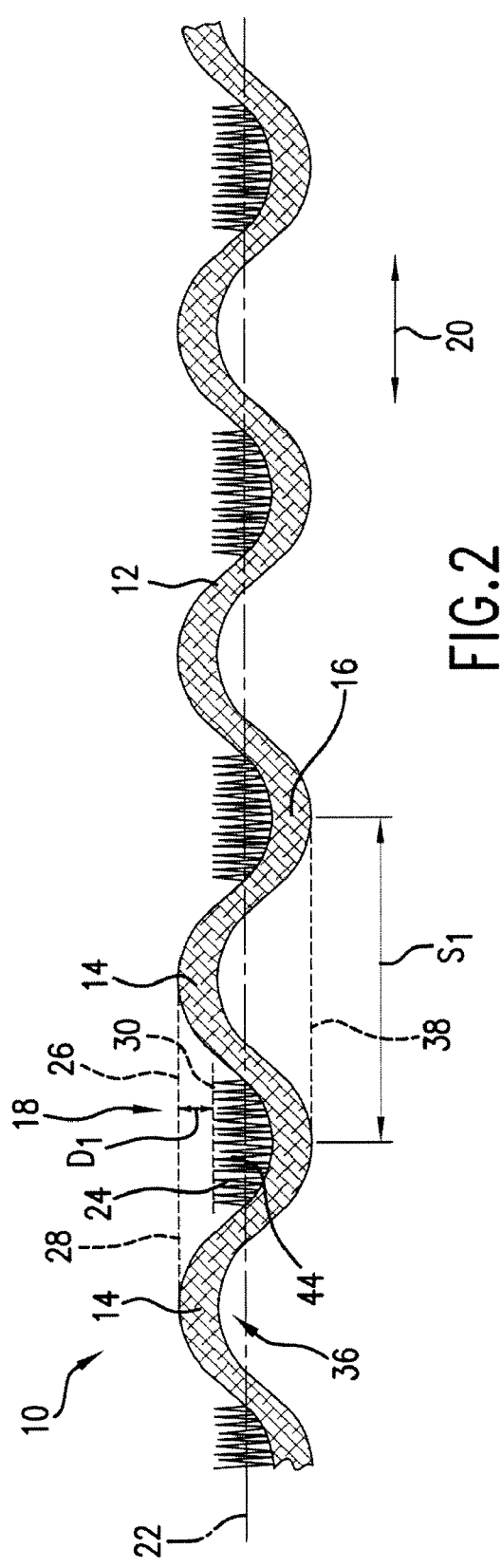
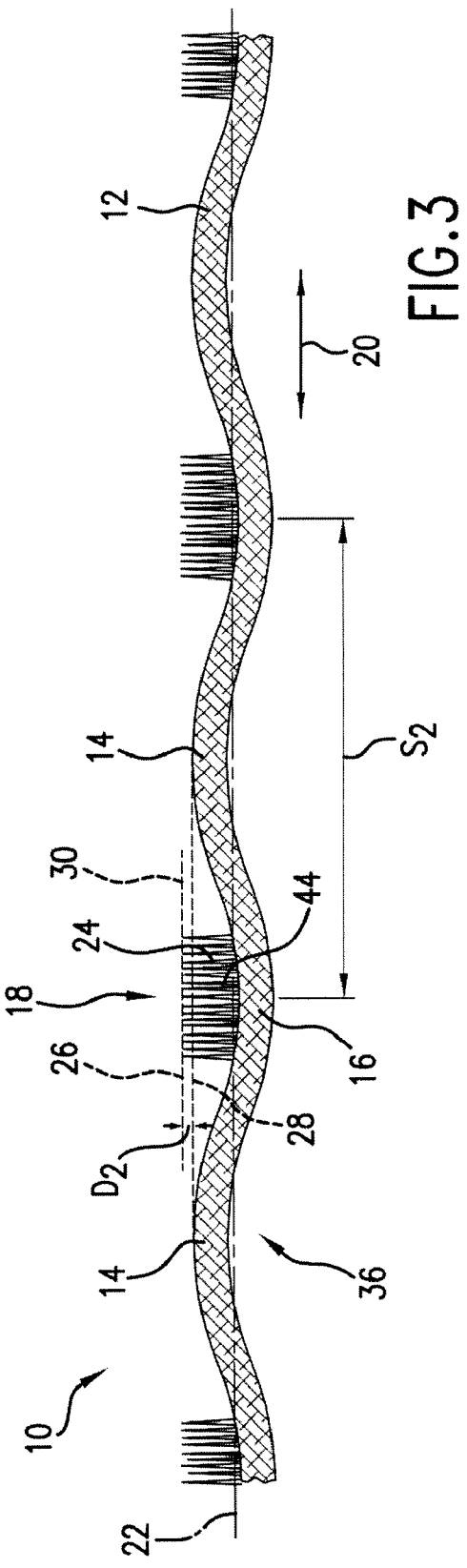

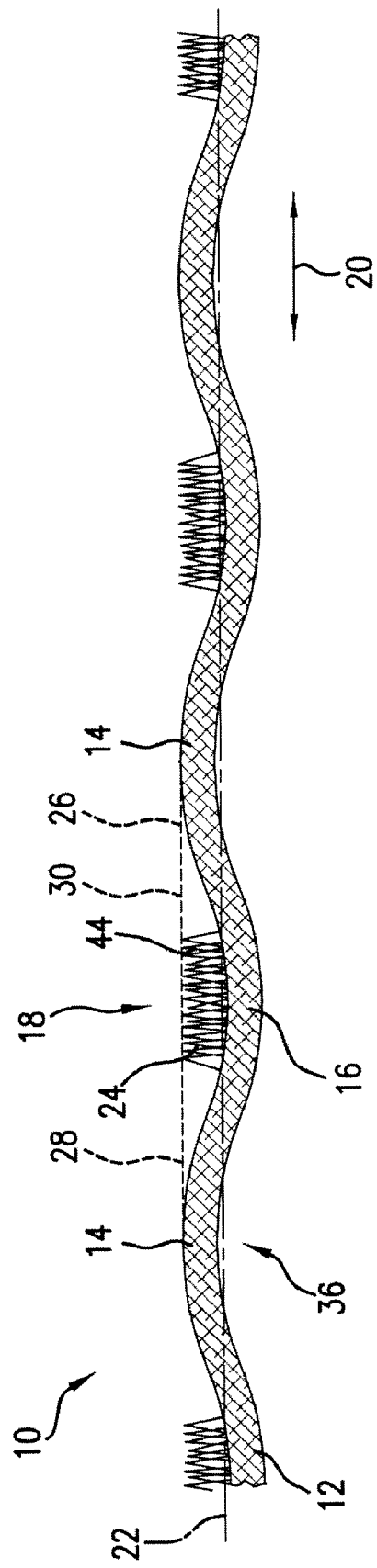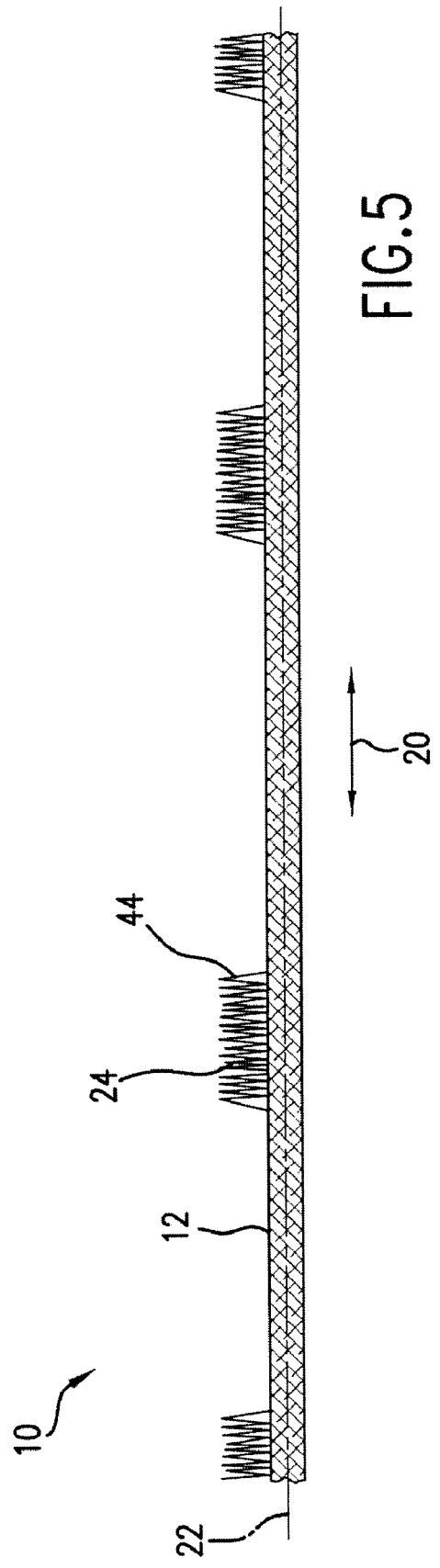

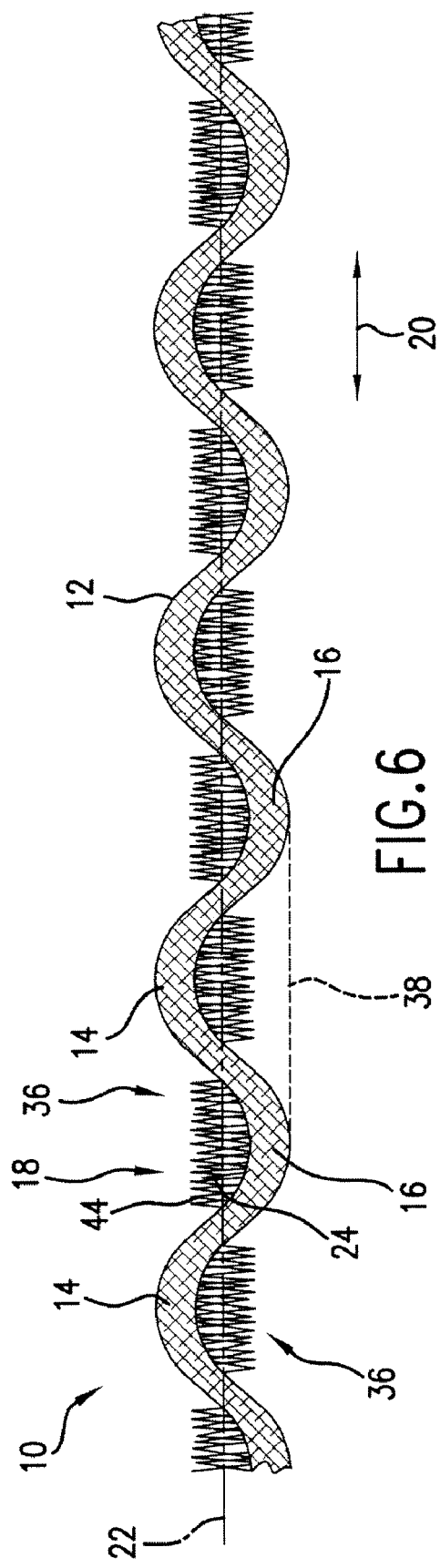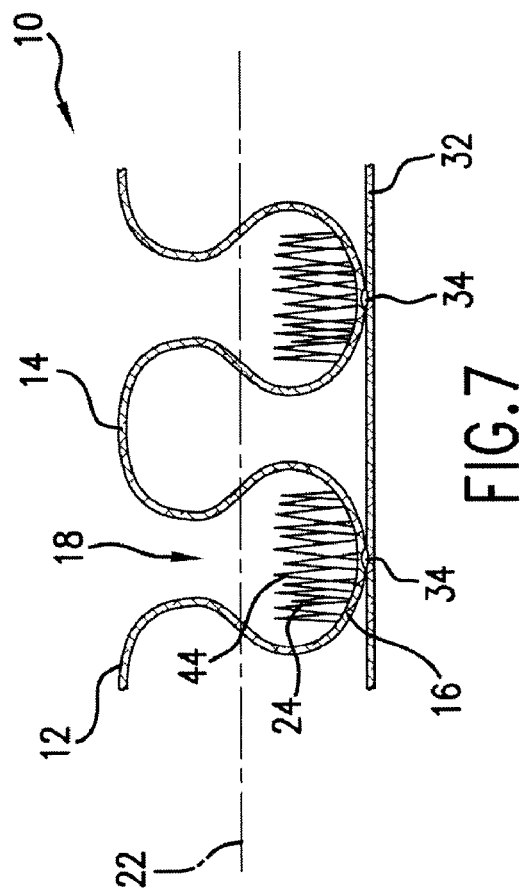

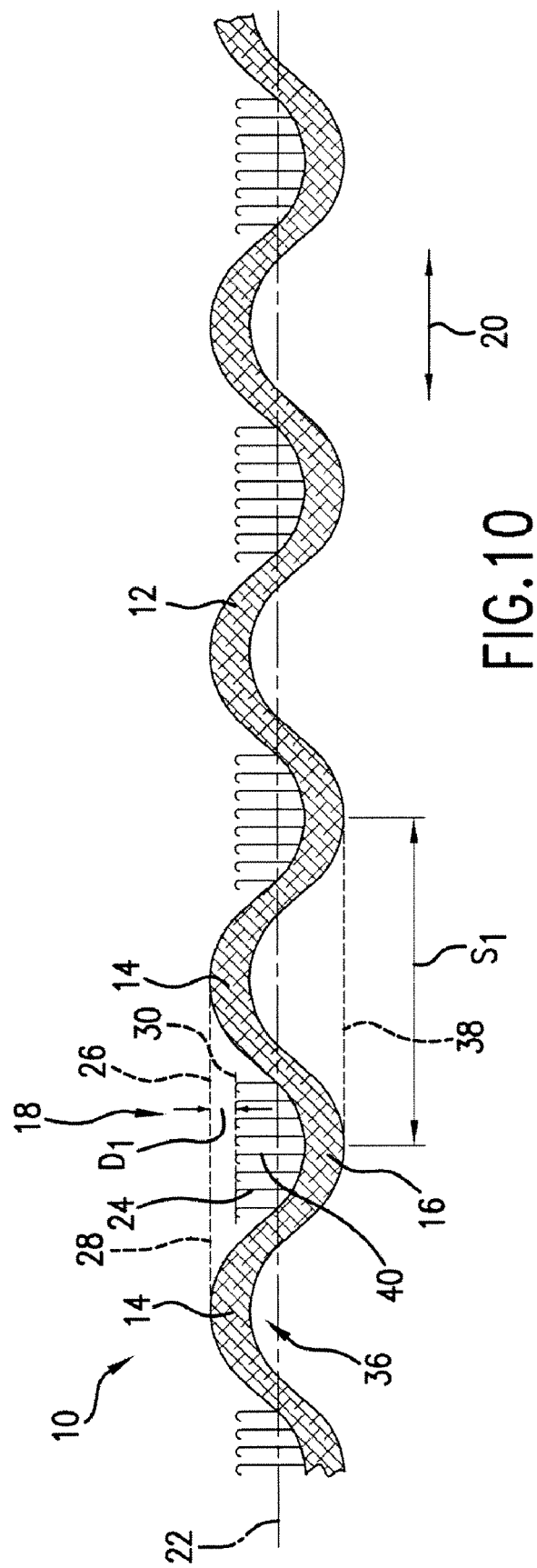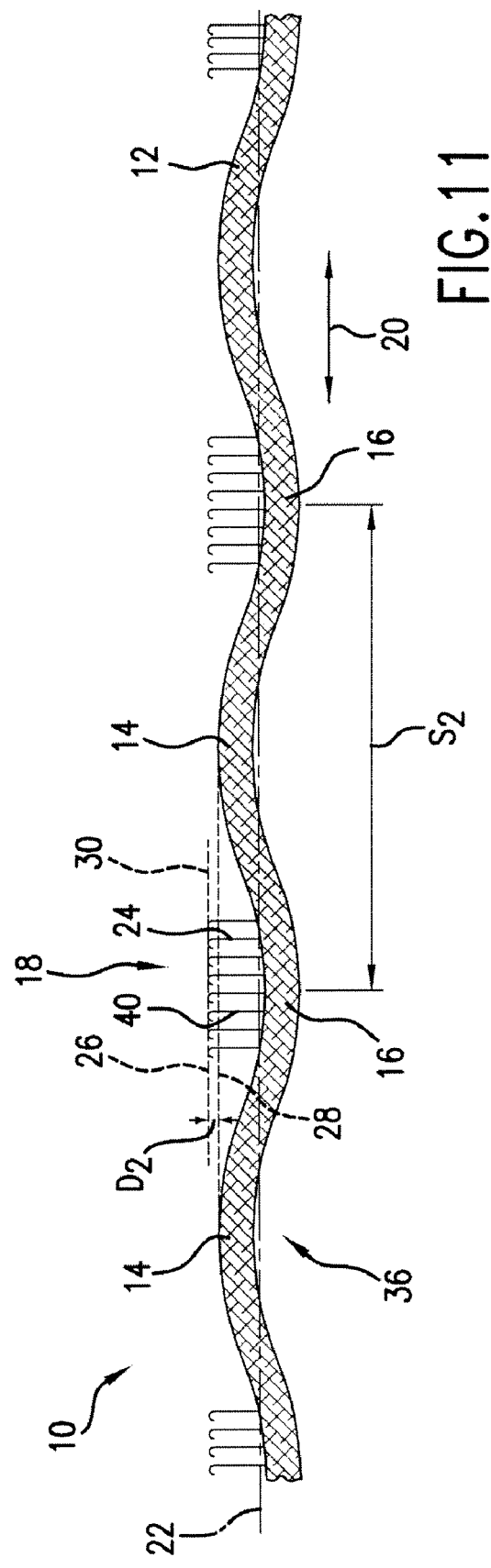

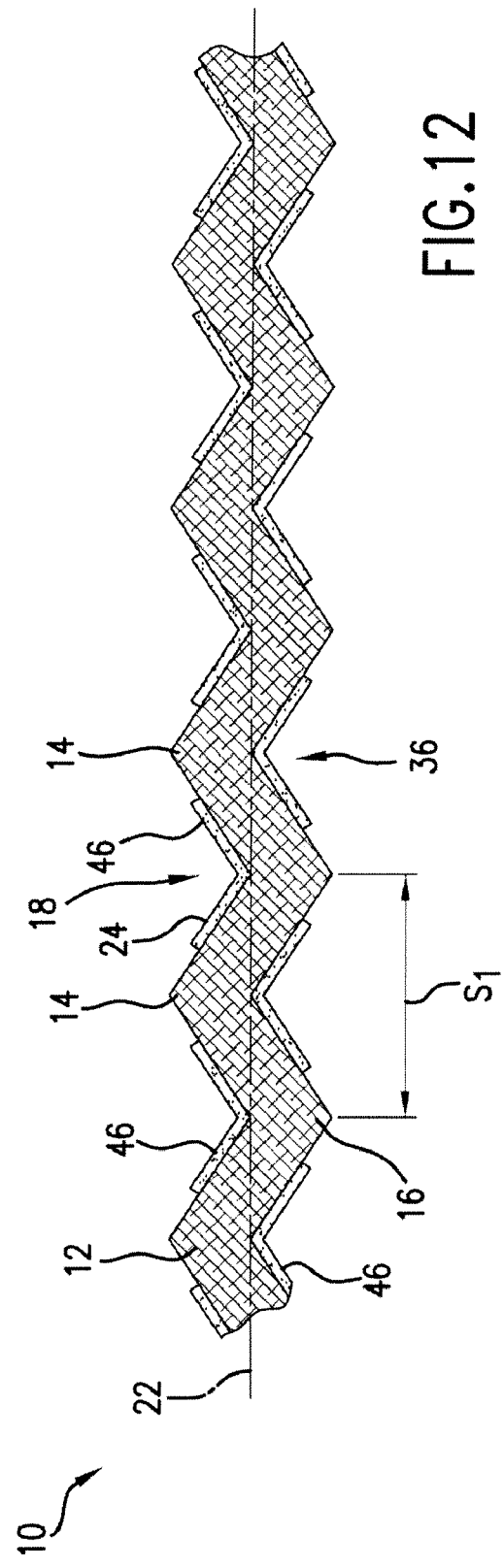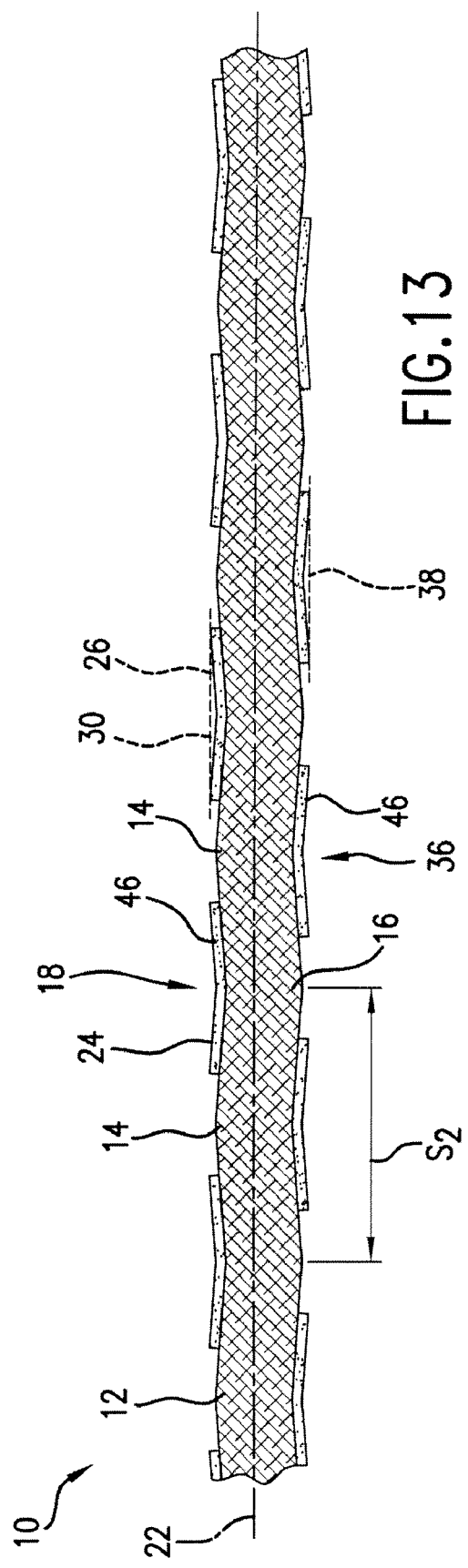

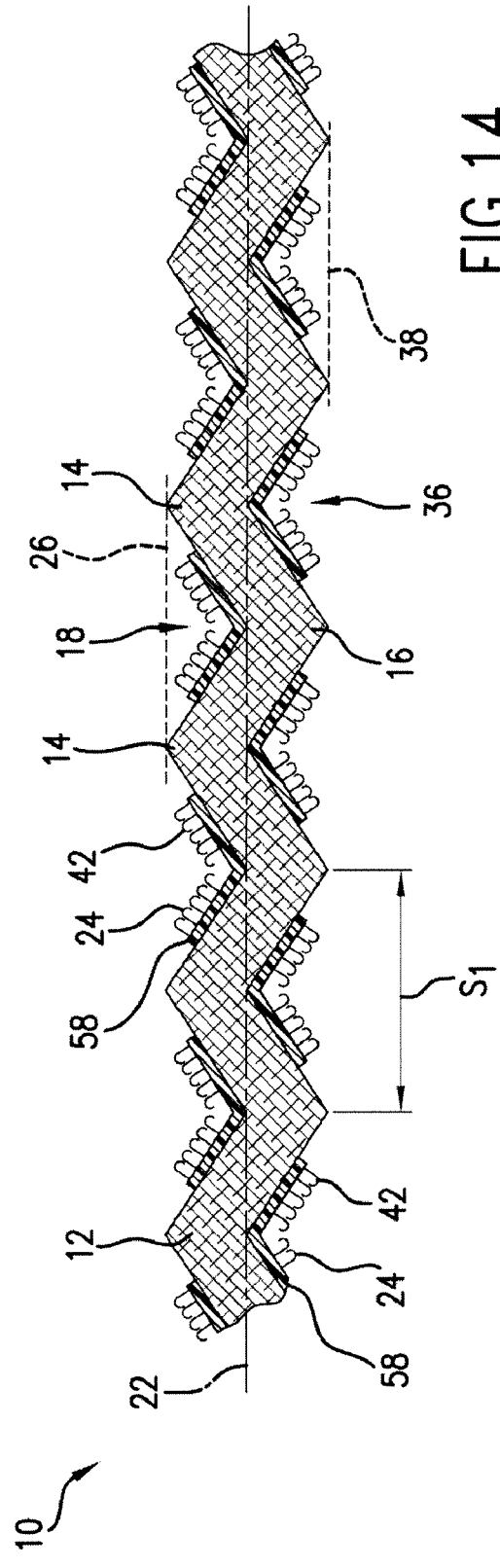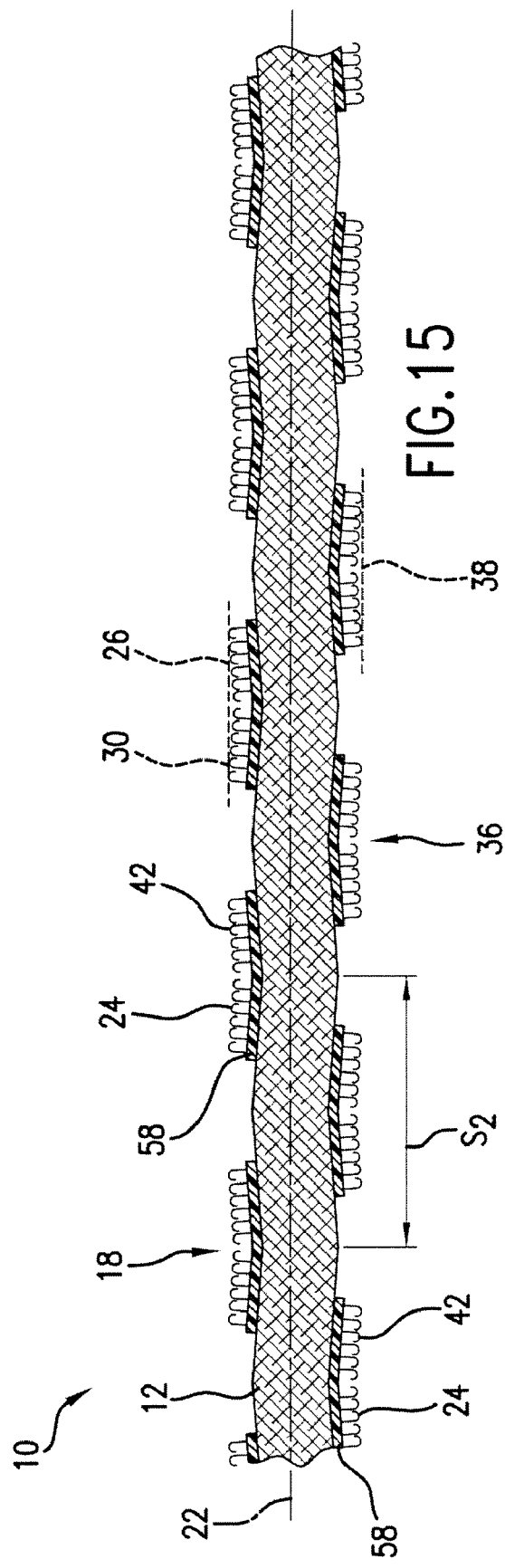

ACTIVATABLE FASTENING SYSTEM AND WEB HAVING ELEVATED REGIONS AND FUNCTIONAL MATERIAL MEMBERS

RELATED APPLICATIONS

The present application is a divisional application and claims priority to U.S. patent application Ser. No. 10/743,556, filed on Dec. 22, 2003.

BACKGROUND

Webs, such as non-woven webs, may be used in a variety of applications. For instance, webs may be used in order to clean surfaces. In such instances, the web may be configured onto a scrubbing brush or mop. The web can have bristles or grit disposed thereon in order to aid in cleaning. The web can be configured as a dry wipe in order to clean the surface, or may be a wet wipe so that the web is wet to some degree when cleaning the surface. The web may also be designed to be a reusable web that can be used in several applications, or may be a disposable web that is of a more limited life.

Alternatively, webs can be used in applications in which the web absorbs fluid or acts as a fluid barrier. For instance, the web can be used in the construction of a diaper. In such instances, the web may have an adhesive or other fastener, such as a hook and loop type fastener, disposed thereon in order to secure the web either to itself or to some other component. The adhesive or other fastener is located on the surface of the web and effects attachment once contact with a complementary surface or object occurs.

As such, webs are designed in order to have functional members disposed thereon in order to accomplish such tasks as cleaning and fastening. However, the positioning of the functional members on the web is such that they will function whenever the web comes into contact with a complementary surface or object. This is the case even if the user does not intend to employ the functional member.

For instance, a web that has a scrubbing material, such as grit, disposed onto a portion of the web may be used to clean a soft surface. The user may inadvertently scratch the surface should the scrubbing material contact the surface by mistake. Additionally, a web with a fastening element disposed thereon will adhere to surfaces the fastening material contacts, even if it is not the intent of the user to attach the fastening element.

SUMMARY

Various features and advantages of the invention will be set forth in part in the following description, or may be obvious from the description.

The present invention provides for a web for use in applying a functional material. The web includes a layer that has a plurality of elevated regions. The layer defines a plurality of cavities that are located between adjacent elevated regions. The layer has a plurality of depressed regions located intermediate the elevated regions. The layer has a longitudinal direction and a longitudinal mid-plane defined therethrough. The web also includes a plurality of functional material members that are located in the cavities of the layer. The functional material members are capable of having particles or surfaces adhere thereon. The layer is extendable in the longitudinal direction so that the elevated regions are moved in a direction towards the longitudinal mid-plane.

The present invention also provides for a web that is used in applying a functional material. The web includes a layer having a first side and a remote second side that has a plurality of alternating elevated and depressed regions on the first side of the layer. The layer defines a plurality of cavities that are each between two successive elevated regions. The layer has a longitudinal direction and a longitudinal mid-plane defined therethrough. A plurality of functional material members are included and are located in the cavities of the layer. The layer has a first orientation and a second orientation. The elevated regions are positioned generally closer to the longitudinal mid-plane when the layer is in the second orientation, as opposed to the configuration where the layer is in the first orientation.

The present invention also provides for a web as discussed above where the elevated regions define the uppermost portion of the layer before the layer is extended, and where the functional material members define the uppermost portion of the layer after the layer is extended. Alternatively, the present invention provides for a web as set forth above where the elevated regions still define the uppermost portion of the layer, even after the layer is extended.

Also, included in accordance with the present invention is a web as set forth above where the web has a reinforcing layer. The reinforcing layer is attached to the depressed regions of the layer that has the plurality of elevated regions.

The present invention also provides for a web as previously discussed where the layer that has the plurality of elevated regions defines a plurality of cavities that are located between adjacent depressed regions, the cavities being generally on second side of the layer. Also, the plurality of functional material members are located in the cavities that are between both the adjacent depressed regions on the second side of the layer, and the cavities between the adjacent elevated regions on the first side of the layer.

Further exemplary embodiments of the present invention exist where the functional material members are various elements. For instance, the present invention provides for embodiments where the functional material members are hooks of a hook and loop fastener system, loops of a hook and loop fastener system, hooks that are configured for retaining objects thereon, abrasive members that are more abrasive than the layer, a tacky adhesive, a pressure-sensitive adhesive, a thermally activatable adhesive, and/or a gecko-like adhesive. In an alternate embodiment, the functional members of webs of the present invention do not include an adhesive, or do not include any one or more of a tacky adhesive, a pressure-sensitive adhesive, a thermally activatable adhesive, and a gecko-like adhesive. In another alternate embodiment, the functional members do not include hook materials.

The present invention provides for exemplary embodiments of the web as discussed above where the layer is extendable in the longitudinal direction in a variety of manners. In one exemplary embodiment, the layer is extendable by a temperature difference that is imparted onto the layer. Additionally or alternatively, the present invention provides for an exemplary embodiment where the layer is made from a water sensitive material. In this instance, the layer is extendable in the longitudinal direction when water is imparted onto the layer. Extension can also be achieved by applying tension to the web, such as by the action of hands pulling on the layer or tension forces in use due to body movement.

Alternatively, a flexing portion of a web may be restrained from further extending in a longitudinal direction by rigid or semi-rigid materials around the portion of the web, yet the portion of the web may be able to flex between two orientations, a recessed orientation and an elevated orientation. The flexing portion of the web may be capable of extension in a longitudinal direction if the rigid or semi-rigid restraining material were removed. The flexing portion has functional members thereof such as adhesive or hooks, wherein the functional members are more capable of engaging an opposing surface when the flexing portion is in an elevated orientation than in a recessed orientation. The flexing portion generally has a degree of curvature which may extend in one or more directions. Specifically, the curvature of the flexing portion may resemble a simple arc with curvature in one direction, or may have two-dimensional curvature in the form of a dome or other structure with two-dimensional curvature capable of being pushed or, in some cases, "snapped," between two stable orientations, corresponding to recessed and elevated orientations. An "elevated" orientation generally refers to the flexing portion moving away from the plane of the surrounding web and toward an opposing surface for possible engagement.

The present invention provides for exemplary embodiments of the web as set forth above where the extendability of the layer in the longitudinal direction is either reversible or irreversible.

Additionally, the present invention provides for exemplary embodiments of the web as discussed above where the layer is extendable such that the layer assumes a generally flat shape, and the elevated and depressed regions are neither elevated nor depressed. In this configuration, the plurality of cavities defined by the layer are no longer present.

The present invention also provides for a web that is used in applying a functional material. The web has a layer with a plurality of elevated regions and a plurality of cavities defined between adjacent elevated regions. The layer also has a plurality of depressed regions located intermediate the elevated regions. The cross-sectional shape of the layer is generally sinusoidal. The layer has a longitudinal direction, and a longitudinal mid-plane defined therethrough. The web also includes a plurality of functional material members that are located in the cavities of the first layer. The functional material members can be hooks of a hook and loop fastener system. The layer can be both extendable and retractable in the longitudinal direction. Before the layers are extended in the longitudinal direction, the elevated regions define the uppermost portion of the layer. Extension of the layer in the longitudinal direction causes the elevated regions to be moved in a direction towards the longitudinal mid-plane. After the layer is extended, the functional material members then define the uppermost portion of the layer.

In a related embodiment, the web is extendable in both a longitudinal direction and a lateral direction normal to the longitudinal direction. Extension in either the longitudinal or lateral direction can result in relative elevation of functional members to activate the ability of the web to attach to another object. Such a web may have a dimpled structure with a plurality of spaced apart depressions, and may have sinusoidal cross-sections in either the longitudinal or lateral direction, or, alternatively, may be a substantially planar web with spaced apart domes having functional members therein that can be "popped" or inverted from a recessed orientation to an elevated orientation in which the functional members in the dome are facing outward for engagement with an opposing surface.

Also provided for in accordance with the present invention is an article that has an activatable fastener and is configured to be worn by a user. The article includes a body portion with a first surface and a second surface opposite therefrom. A fastening member is attached to the body portion and has a recessed orientation in which the fastening member is positioned below the first surface of the body portion. The fastening member also has an elevated orientation in which the fastening member is positioned above the first surface of the body portion. The fastening member is engageable with the body portion in order to help retain the body portion on the user. The fastening member is more easily engageable with the body portion when in the elevated orientation than when in the recessed orientation.

Also included in accordance with the present invention is an article as immediately discussed in which the fastening member is a plurality of hooks. The body portion has a plurality of loops that are located on the second surface, and the hooks are engageable with the loops in order to help retain the body portion on the user.

The present invention also provides for an activatable fastening system that includes a plurality of hooks from a hook and loop type fastener. The hooks have an activated orientation in which the hooks are engageable with the loops from a hook and loop type fastener in order to be retained thereon. The hooks also have a deactivated orientation in which the hooks are less engageable with the loops than when in the activated orientation. The activatable fastening system also includes an actuation member that is engageable with the hooks. The actuation member is activatable by a user so that the actuation member repositions the plurality of hooks between the activated orientation and the deactivated orientation.

Also included in accordance with the present invention is an activatable fastening system as immediately discussed wherein the deactivated orientation, the actuation member reduces the amount of curvature of the hooks. Alternatively, the activatable fastening system may be configured so that in the deactivated orientation the actuation member shields a portion of the hooks from the loops. In accordance with one exemplary embodiment of the present invention, the actuation member is a wire-like frame made of metal or plastic that engages the outer surface of the hooks, while in another exemplary embodiment of the present invention the actuation member has a rigid portion that is disposed in hollow interiors of the hooks and when actuated repositions the hooks to the deactivated orientation so that the curvature of the hooks is reduced.

BRIEF DESCRIPTION OF THE DRAWINGS

FIG. 2 is a partial cross-sectional view of the web of FIG. 1. The web is shown in an unextended state.

FIG. 3 is a partial cross-sectional view of the web of FIG. 1. The web is shown in an extended state in which the abrasive material defines the uppermost portion of the layer of the web.

FIG. 4 is a partial cross-sectional view of the web of FIG. 1. The web is shown in an extended state in which elevated regions of a layer of the web and the plurality of functional material members define the uppermost portion of the layer.

FIG. 5 is a partial cross-sectional view of the web of FIG. 1. The web is shown in an extended state in which the elevated and depressed regions of the web are no longer elevated or depressed, and a layer of the web assumes a generally straight cross-sectional shape.

FIG. 6 is a partial cross-sectional view of an alternative exemplary embodiment of the web in accordance with the present invention. Here, the web has a plurality of functional material members disposed in cavities defined between adjacent depressed regions of the layer of the web.

FIG. 7 is a partial cross-sectional view of an alternative exemplary embodiment of the web in accordance with the present invention. A reinforcing layer is present and is bonded to depressed regions of the layer of the web.

FIG. 10 is a partial cross-sectional view of the web of FIG. 9. The web is shown in an unextended state.

FIG. 11 is a partial cross-sectional view of the web of FIG. 9. The web is shown in an extended state in which the hooks define the uppermost portion of the layer of the web.

FIG. 12 is a partial cross-sectional view of a web in accordance with one exemplary embodiment of the present invention. The web is shown as having functional material members disposed in cavities which are defined between adjacent elevated regions and adjacent depressed regions of the layer.

FIG. 13 is a partial cross-sectional view of the web of FIG. 12. Here, the web is shown in an extended state in which the functional material members define an uppermost and lowermost portion of the layer of the web.

FIG. 14 is a partial cross-sectional view of a web in accordance with one exemplary embodiment of the present invention. A plurality of functional material members, which are hooks, are disposed in cavities defined between adjacent elevated regions and adjacent depressed regions of the web.

FIG. 15 is a partial cross-sectional view of the web described in FIG. 14 in which the web is shown in an extended state. Here, the hooks define both the uppermost portion and lowermost portion of the layer of the web.

DETAILED DESCRIPTION

Figure 1:
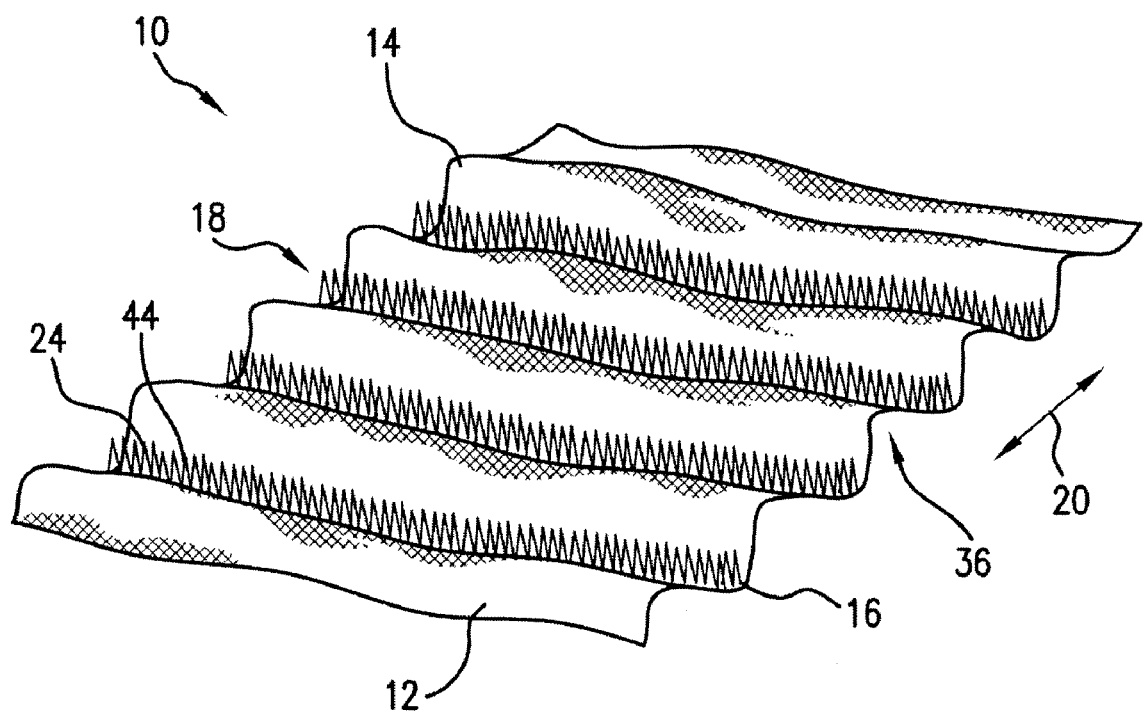
FIG. 1 is a perspective view of a web in accordance with one exemplary embodiment of the present invention. The web has a plurality of functional material members that are an abrasive material disposed thereon.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges and limits mentioned herein include all ranges located within, and also all values located under or above the prescribed limits. For instance, a range of from 100 to 200 also includes ranges from 100 to 150, 170 to 190, and 153 to 162. Further, a limit of up to about 7 also includes a limit of up to about 5, up to 3, and up to about 4.5.

The present invention provides for a web 10 that may be reoriented from a first to a second orientation such that functional material members 24 which are disposed on a layer 12 of the web 10 may be repositioned with respect to the layer 12 so that they are capable of being used by a user of the web 10. As such, the web 10 may have an orientation in which the functional material members 24 are not used, and may have another orientation in which the functional material members 24 are positioned so that they can be employed by the user. Such a configuration of the web 10 allows for a duel functionality of the web 10, and also helps to prevent the use of the functional material members 24 until such time the user actually desires to use the functional material members 24.

An exemplary embodiment of the web 10 used in accordance with the present invention is shown in FIG. 1. Here, the web 10 is shown as being formed by a single layer 12. However, it is to be understood that in accordance with other exemplary embodiments of the present invention that any number of layers 12 may be employed, and the present invention is not limited to a web 10 that employs only a single layer 12. The layer 12 is formed from a plurality of alternating elevated regions 14 and depressed regions 16. FIG. 2 shows a cross-sectional view of the web 10 of FIG. 1. Here, the alternating elevated regions 14 and depressed regions 16 of the layer 12 form a web 10 that has a generally sinusoidal shape.

As can be seen, the layer 12 defines a plurality of cavities 18 which in this exemplary embodiment of the present invention are located between adjacent elevated regions 14 of the layer 12. The layer 12 also defines a plurality of cavities 36 that are located between adjacent depressed regions 16.

The web 10 is provided with a plurality of functional material members 24 which in the exemplary embodiments shown in FIGS. 1-6 are abrasive members 44. The functional material members 24 are located in the cavities 18. The functional material members 24 may be attached to the layer 12 in a variety of manners as is commonly known to those skilled in the art. For instance, the functional material members 24 may be attached via adhesion, mechanical fasteners, sonic welding, or may be integrally formed with the layer 12. It is to be understood that the present invention is not limited to a particular type of attachment between the functional material members 24 and the layer 12.

The web 10 has a longitudinal mid-plane 22 defined therethrough which extends in a longitudinal direction 20 through the web 10. With reference to the longitudinal mid-plane 22, the layer 12 has an uppermost portion 26 located on one end thereof, and a lowermost portion 38 location on an opposite end thereof. In the orientation of the layer 12 shown in FIG. 2, the elevated regions 14 define the uppermost portion 26 of the web 10, and the depressed regions 16 define the lowermost portion of the layer 12. As such, the user may move the web 10 across a surface such that only the elevated regions 14 or the depressed regions 16 of the layer 12 contact the surface.

Also as shown in FIG. 2, the functional material members 24 have a maximum functional material member height 30. Likewise, the elevated regions 14 have a maximum elevated region height 28, which in the configuration shown in FIG. 2 is the same as the uppermost portion 26 height of the web 10. The distance between the maximum functional material member height 30 and the maximum elevated region height 28 is shown as reference numeral $D_1$. Due to fact that the maximum function material height 30 is below the maximum elevated region height 28, the functional material members 24 will not contact a surface when the web 10 is moved across the surface. This is because the functional material members 24 are recessed within the layer 12 a distance $D_1$ from the uppermost portion 26 of the web 10.

FIG. 3 shows the web 10 of FIG. 2 in which the layer 12 of the web 10 is elongated in the longitudinal direction 20. The amount of elongation may be measured, for instance, by comparison of the distance $S_1$ between adjacent depressed regions 16 of the layer 12 in FIG. 2 to the distance $S_2$ between adjacent depressed region 16 of the layer 12 shown in FIG. 3. Elongation in the longitudinal direction 20 has the effect of moving both the elevated regions 14 and the depressed regions 16 closer towards the longitudinal mid-plane 22 of the web 10. In effect, the layer 12 assumes a generally straighter cross-sectional shape once elongated.

The elongation of the layer 12 may be to an extent such that the uppermost portion of the web 10 is no longer defined by the elevated regions 14, but is instead defined by the maximum functional material member height 30. In such an instance, the maximum elevated region height 28 is located closer to the longitudinal mid-plane 22 than the maximum functional material height 30. The difference between the maximum elevated region height 28 and the maximum functional material member height 30 is shown as $D_2$ in FIG. 3. In this configuration, when the web 10 is moved across a surface by a user, the surface will be contacted by the functional material members 24 instead of the situation in FIG. 2 in which the surface is contacted by the elevated regions 14. As such, the web 10 of the present invention demonstrates a duel functionality in which the orientation of the web 10 may be modified such that different portions of the web 10 may be used in order to contact a surface in order to provide different types of functionality.

For instance, the web 10 may be used in accordance with the configuration in FIG. 2 in order to clean a surface by contact with the elevated regions 14 or depressed regions 16, and then placed into the orientation shown in FIG. 3 in which certain portions of the surface may be scrubbed by the functional material members 24 which in this instance are abrasive members 44. The orientation in FIG. 2 allows for the abrasive members 44 to be located at distance $D_1$ away from the surface to be cleaned in order to eliminate the possibility of scratching the surface, should the surface that is being cleaned be soft enough to be damaged by the abrasive members 44.

The present invention includes various exemplary embodiments in which the orientation of the web 10 may be modified in order to change the functionality of the web 10. For instance, FIG. 4 shows an alternative orientation in which both the functional material members 24 and the elevated regions 14 define the uppermost portion 26 of the web 10. In this instance, both the functional material members 24 and the elevated regions 14 will contact the surface when the web 10 is moved across the surface by a user. In such an orientation, the user will be able to employ both the functionality of the elevated regions 14 and the functional material members 24 simultaneously.

The elongation of the layer 12 may be taken to any degree. For instance, FIG. 5 shows a configuration in which the layer 12 is elongated to its maximum extent. In such an instance, the cross-sectional shape of the layer 12 is generally straight. The elevated regions 14 and the depressed regions 16 are no longer distinguishable as being features of the layer 12. Additionally, the cavities 18, 36 are also no longer distinguishable in the layer 12.

Although described as being extendable, it is to be understood that the layer 12 of the present invention may be thought of as being either extendable or compressible. As such the layer 12 may begin in the orientation shown in FIG. 3, and then may be compressed in the longitudinal direction 20 in order to be placed into the orientation shown in FIG. 2. Further, the layer 12 is compressible in the longitudinal direction 20 to an extent greater than that shown in FIG. 2. For instance, the layer 12 may be compressible (i.e., contractible, which may be due to elastic properties of the layer 12 or due to its ability to be mechanically foreshortened) in the longitudinal direction 20 to such an extent that the elevated regions 14 contact one another. Therefore, the present invention includes various exemplary embodiments where the layer 12 is compressible or extendable in the longitudinal direction to any degree.

The present invention is not limited to having a specific amount of functional material members 24 located thereon. Further, the location of the functional material members 24 on the layer 12 may be varied in accordance with other exemplary embodiments of the present invention. For instance, FIG. 6 shows an exemplary embodiment where additional functional material members 24 are located in the cavities 36 between depressed regions 16. Extension of the layer 12 in the longitudinal direction 20 will cause the depressed regions 16 to move towards the longitudinal mid-plane 22. In such a situation, the layer 12 may be elongated to such a degree that the functional material members 24 therefore define the lowermost portion 38 of the layer 12. The interaction between the functional material members 24 located in the cavities 36 between the depressed regions 16 may be the same as that previously discussed above with respect to the functional material members 24 located in the cavities 18 between elevated regions 14. Such additional functional material members 24 allow for an even greater degree of functionality with the web 10 due to the fact that the functional material members 24 may be located on either side of the layer 12.

With reference to FIGS. 2 and 3, the maximum functional material member height 30 is located a distance $D_1$ from the maximum elevated region height 28 which forms the uppermost portion 26 of the layer 12. At this point, the depressed regions 16 are located a distance $S_1$ from one another. The distance $S_1$ may be the distance between the apex or lowest point of adjacent depressed regions 16. The distance $D_1$ may be the distance between the maximum functional material member height 30 and the apex or uppermost portion of the elevated regions 14.

Elongation of the layer 12 causes the distance between the depressed regions 16 to increase to a distance $S_1$ as shown in FIG. 3. In this instance, the elevated regions 14 are moved closer to the longitudinal mid-plane 22 such that the maximum functional material member height 30 is further from the longitudinal mid-plane 22 than the maximum elevated region height 28 of the elevated regions 14, this distance being a distance $D_2$.

When configured as a scrubbing product, the elevated regions 14 provide a certain degree of softness, absorption, and/or act as a buffing agent in cleaning a surface. When activated, the abrasive members 44, which form the functional material members 24, may be used in order to remove ground-in objects on the surface being cleaned, or to otherwise prepare the surface for a future treatment. The web 10 may be activated as a result of an action of the user, for instance the layer 12 may be stretched or compressed by the user in order to reconfigure the web 10 such that the abrasive members 44 may be employed. Additionally, downward pressure may be imparted onto the depressed regions 16 in order to move the elevated regions 14 closer to the longitudinal mid-plane and in effect cause an elongation of the layer 12 in the longitudinal direction 20.

The layer 12 may have various cross-sectional shapes in accordance with other exemplary embodiments of the present invention. For instance, an alternative exemplary embodiment of the web 10 is shown in FIG. 7. Here, the cross-sectional shape of the layer 12 is shown as being generally mushroom-shaped. Additionally, a reinforcing layer 32 is shown as being attached to the depressed regions 16 of the layer 12 through spot bonds 34. The spot bonds 34 used may be of any type commonly known in the art. For instance, the spot bond 34 may be adhesive, or may be a weld formed by heat and pressure in accordance with various exemplary embodiments. The reinforcing layer 32 may be present in order to provide stabilization to the layer 12, or may be provided in order to retain the layer 12 in a particular orientation.

Figure 8:
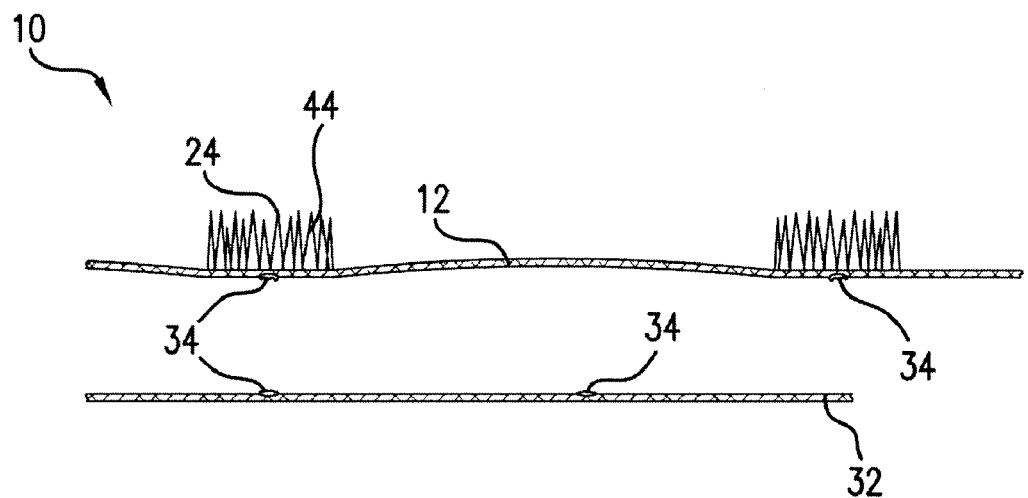
FIG. 8 is a partial cross-sectional view of an exemplary embodiment of the web in accordance with the present invention. Here, as the layer is extended, a reinforcing layer which was attached to the depressed regions is disengaged from the layer.

The reinforcing layer 32 may be elastic in accordance with one exemplary embodiment of the present invention. In this instance, when the layer 12 is elongated, the reinforcing layer 32 will also elongate along with the layer 12. In such an instance, the elevated regions 14 may be moved closer to the longitudinal mid-plane 22 in a manner similar to that described above with respect to the web 10 of FIGS. 2 and 3. Alternatively, the spot bonds 34 and/or the reinforcing layer 32 may be configured in order to break when the layer 12 is elongated. Such a configuration is shown in FIG. 8. Here, the spot bonds 34 are configured in order to break once the layer 12 becomes elongated. The web 10 may be configured such that the reinforcing layer 32 may be reattached to the layer 12 after this elongation. Alternatively, the web 10 may be configured so that the reinforcing layer 32 is designed to be permanently detached from the layer 12 once the layer 12 becomes elongated and the spot bonds 34 are broken.

Figure 9:
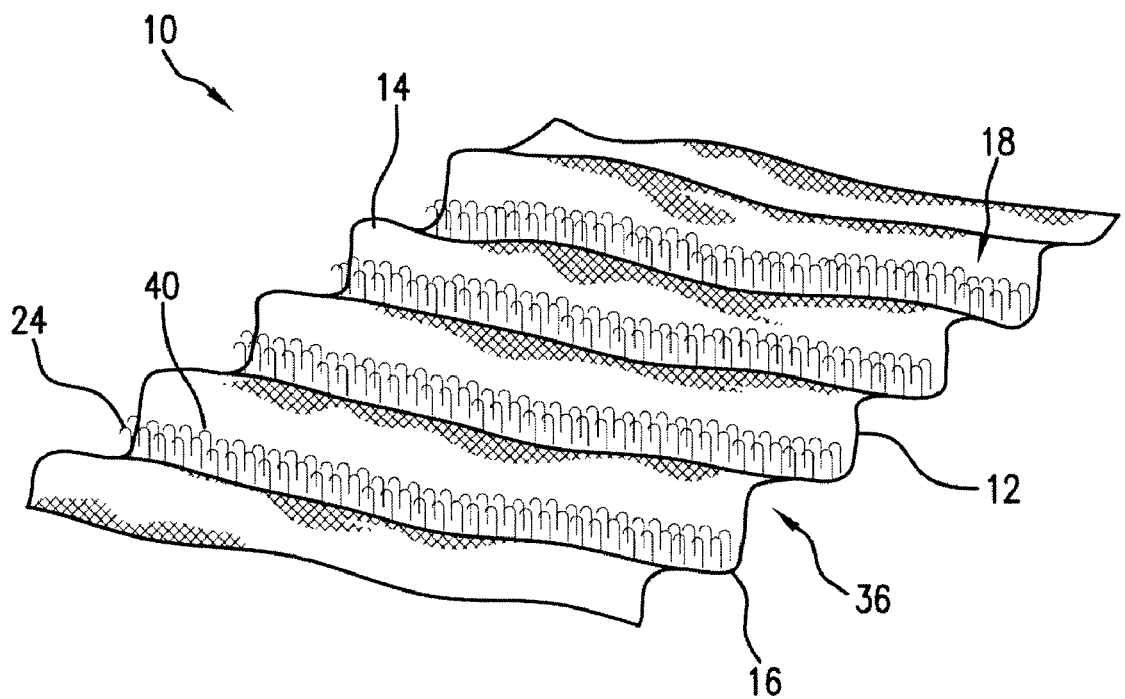
FIG. 9 is a perspective view of an exemplary embodiment of a web in accordance with the present invention. A plurality of functional material members, which are hooks, are disposed on a layer of the web.

Although described as being abrasive members 44, the functional material members 24 may be configured differently in accordance with other exemplary embodiments of the present invention. For instance, FIG. 9 shows an embodiment of the web 10 in which the functional material members 24 are hooks 40 which form a part of a hook and loop type fastener. The hooks 40 may be used in order to engage loop portions (not shown) on another object in order to effect an attachment between the web 10 and this other object. As such, the functional material members 24 may be fastening type elements that are used in order to either permanently or temporarily attach the web 10 to some other object.

FIGS. 10 and 11 are partial cross-sectional views of the web 10 shown in FIG. 9. FIGS. 10 and 11 are similar to FIGS. 2 and 3 in that the layer 12 is shown in an unextended state, and then in an extended state in which the functional material members 24, being hooks 40, define the uppermost portion 26 of the layer 12. In the orientation shown in FIG. 10, the layer 12 may be moved across a surface, and the hooks 40 comprising the functional material members 24, will not be able to engage the surface since the elevated regions 14 of the layer 12 define the uppermost portion 26. Once the layer 12 is extended into the configuration shown in FIG. 11, the hooks 40 may then be able to engage the surface which is contacted since the hook 40 in this orientation define the uppermost portion 26 of the layer 12. Such a web 10 employs a dual functionality in which the web 10 is both attachable to the surface, and non-attachable to the surface.

When used as a mechanical fastening system, the web 10 may have a soft feel due to the fact that the elevated regions 14 form the uppermost portion 26 of the layer 12. When activated, the hooks 40 which form the functional material members 24 may give the outer surface of the web 10 a rough feel and allow for attachment to complementary loops (not shown).

Aside from being hooks 40, the functional material members 24 may be other types of adhesives or components of an adhesive/fastener system in accordance with other exemplary embodiments of the present invention. For instance, FIG. 12 shows an exemplary embodiment of the present invention in which the functional material members 24 are an adhesive 46. The adhesive 46 may be of any type commonly known in the art. For instance, the adhesive 46 may be a tacky adhesive, a heat-activatable adhesive, or a microencapsulated adhesive located in a shell in accord with various exemplary embodiments of the present invention. The adhesive 46 comprising the functional material members 24 may be located both in the cavities 18 located between adjacent elevated regions 14, and in the cavities 36 located between adjacent depressed regions 16 of the layer 12. FIG. 13 shows the web 10 of FIG. 12 in an elongated condition. In such a state, the adhesive 46 which comprises the functional material members 24 defines both the uppermost and lowermost portions 26, 38 of the layer 12. In this configuration, the web 10 acts as a double-sided adhesive web which may be capable of attaching either a surface or object to both sides of the web 10.

The functional material members 24 may be configured in order to be able to retain dirt, lint, dust, or other objects thereon when the web 10 is used. The web 10 may be used to clean a floor or other surface. FIGS. 14 and 15 show an exemplary embodiment of the web 10 in which the functional material members 24 are object retaining hooks 42. The object retaining hooks 42 may be attached to a base 58 that is in turn attached to the layer 12, both in the cavities 18 and 36 which are located between adjacent elevated regions 14 and adjacent depressed regions 16 respectively. With such a web 10, a user may use the web 10 shown in the orientation in FIG. 14 in order to clean a floor. The cleaning action is brought about by contact of either the elevated regions 14 or depressed regions 16 of the layer 12 with the floor. Once the user desires to retain objects such as lint, dust, or dirt onto the layer 12, the layer 12 may be elongated into the orientation shown in FIG. 15 in which the object retaining hooks 42 comprise the uppermost portion 26 or lowermost portion 38 of the layer 12 in order to be in contact with the floor and/or objects that are to be retained thereon. Such a web 10 may find use as a disposable wipe or permanent wipe which is configured onto a mop head of a mop such as a SWIFFER© brand disposable mop manufactured by Procter & Gamble (Cincinnati, Ohio) for either wet or dry cleaning applications. In such an instance, it may be the case that the functional material members 24 which comprise the object retaining hooks 42 are located on only one side of the layer 12.

Should the web 10 be placed on the mop head of a mop, the web 10 may be reoriented by a user applying downward force on the handle of the mop. Reorientation may also be accomplished by stretching the web 10 as it is installed on the mop head, or by wetting the web 10 should the web 10 respond by being elongated or compressed upon contact with water. The object retaining hooks 42, which form the functional material members 24, may be used in capturing particles, hair, and/or other coarse objects that would normally not be picked up by the layer 12 should the layer 12 be made of, for instance, a smooth nonwoven material.

Figure 16:
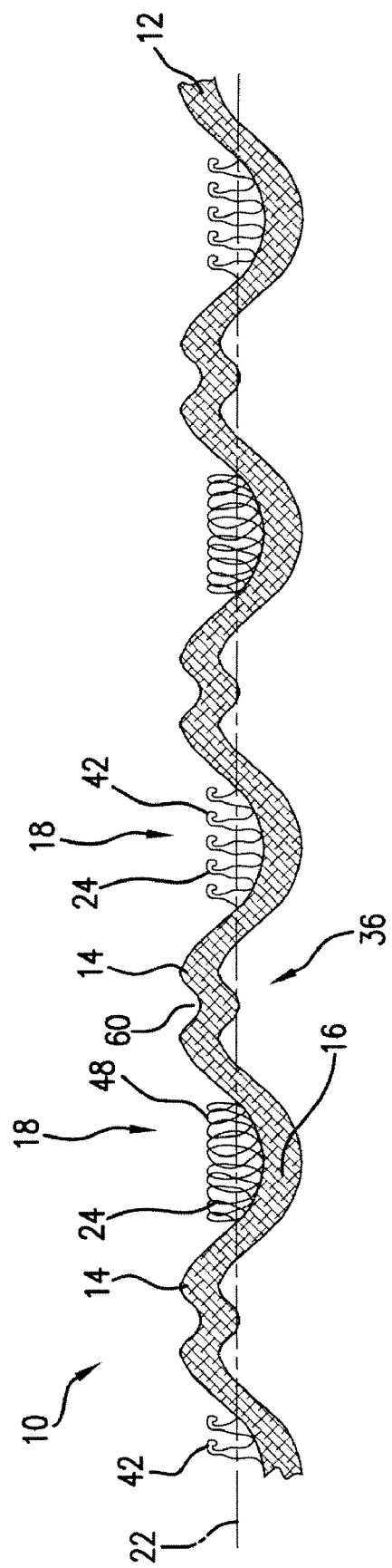
FIG. 16 is a partial cross-sectional view of a web in accordance with one exemplary embodiment of the present invention. A plurality of functional material members, which are loops from a hook and loop fastener system and hooks which are capable of retaining objects thereon, are disposed thereon.

FIG. 16 shows an alternative exemplary embodiment of the web 10 in which different types of functional material members 24 are attached to the layer 12. Here, loops 48 from a hook and loop type fastener are disposed in certain cavities 18 located between elevated regions 14. Additionally, object retaining hooks 42 are located in other cavities 18 located between adjacent elevated regions 14. It is therefore the case that the functional material members 24 do not need to be of the same type, and various types of functional material members 24 may be employed in the web 10. Additionally, the layer 12 is provided with a plurality of dimples 60. The dimples 60 are located in the elevated regions 14 of the layer 12. The dimples 60 may allow for a certain degree of structural rigidity in the layer 12 when the layer 12 is extended. This additional structural rigidity may help to control the movement of the elevated regions 14 towards the longitudinal mid-plane 22, hence controlling the activation or non-activation of the functional material members 24.

Figure 17:
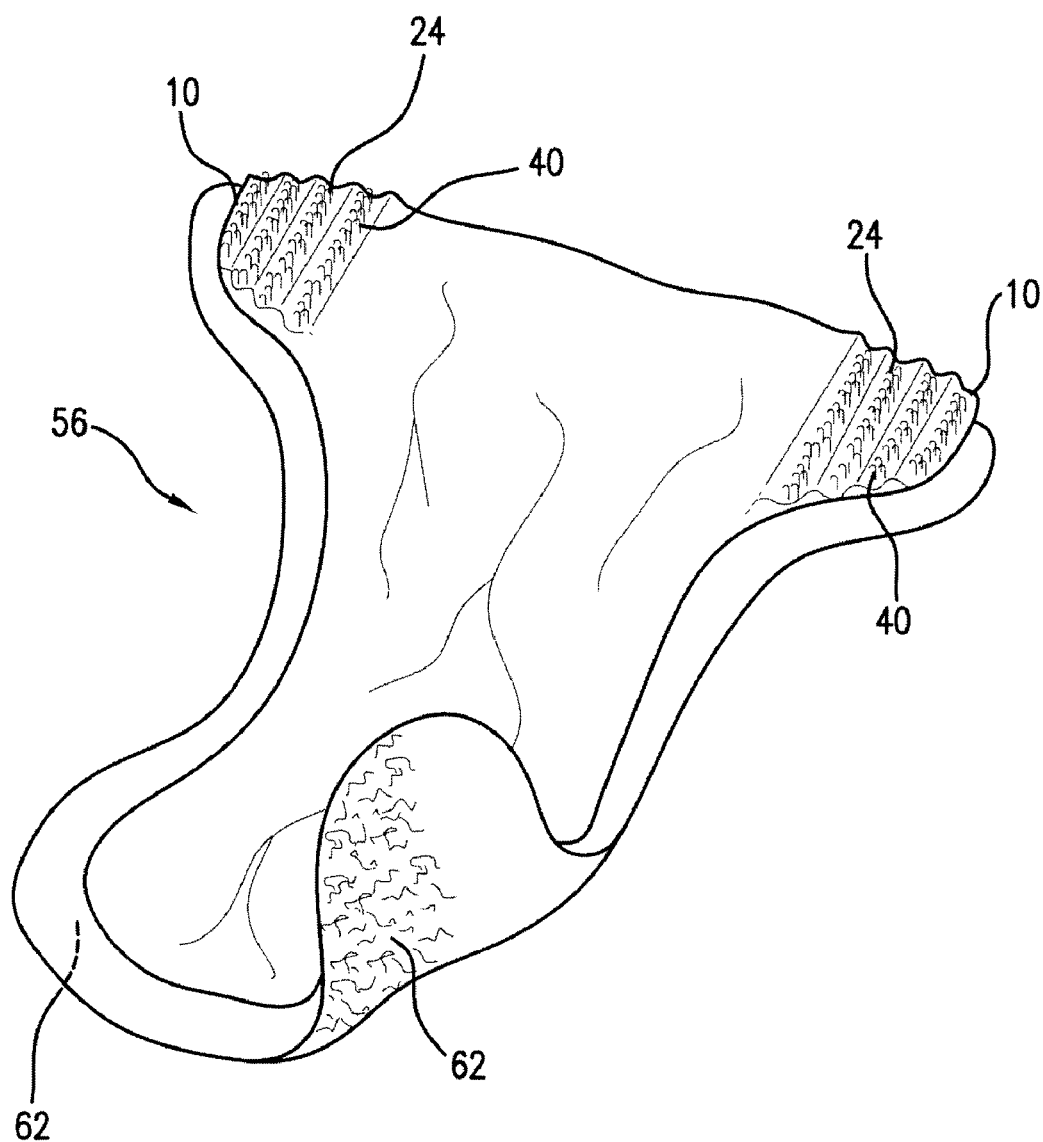
FIG. 17 is a perspective view of a diaper employing a web in accordance with one exemplary embodiment of the present invention.

One application in which the web 10 of the present invention may be employed is shown in FIG. 17. Here, the web 10 includes functional material members 24 which are hooks 40 of a hook and loop type fastener system. The web 10 is used as an attachment for a diaper 56. In this instance, the diaper 56 is provided with one or more loop members 62 which are complementary to the hooks 40 located on the layer 12 of the web 10. The web 10 may be oriented so that the hooks 40 are capable of engaging the loop members 62 and effecting attachment of the diaper 56. As such, the web 10 may contact the loop member 62 without effecting attachment of the diaper 56 until the user desires the diaper 56 to be attached. At such time, the user may place the web 10 into an orientation which makes it possible for the hooks 40 to engage the loop members 62.

The present invention includes various exemplary embodiments in which the functional material members 24 do not need to define the uppermost portion 26 of the layer 12 in order to provide additional functionality to the web 10. For instance, with reference to FIG. 10 the hooks 40 which form the functional material members 24 may still work in order to engage complementary loop members even though they are recessed a distance $D_1$ from the uppermost portion 26 of the web 10. In these instances, the complementary loops may be arranged so that they are insertable into the cavity 18. Also, the web 10 shown in FIG. 10 may be configured in order to have a dual simultaneous functionality. In this instance, the elevated regions 14 may contact the surface to be cleaned, while at the same time the hooks 40 may provide some degree of attachment for the web 10. As such, the present invention includes exemplary embodiments in which the functional material members 24 may provide some degree of functionality, even if not 100%, in instances in which the maximum functional material member height 30 is the same as the maximum elevated region height 28 or is located some distance $D_1$ from the uppermost portion 26 of the layer 12.

Movement of the layer 12 in the longitudinal direction 20 may be accomplished in a variety of manners in accordance with the present invention. For instance, the layer 12 may be stretched at both ends or at one end in order to elongate the layer 12 in the longitudinal direction 20. Downward pressure on the depressed regions 16 may also be used to elongate the web 10. Alternatively, the layer 12 may be compressed in the longitudinal direction 20 in order to reorient the web 10. Also, the web 10 may be heated or cooled in order to effect the elongation or compression of the layer 12 in the longitudinal direction 20. Further, the layer 12 or other components of the web 10 may be made of a water-sensitive material that either expands, shrinks, relaxes, or dissolves when water is imparted thereon. As stated, the elongation or compression in the longitudinal direction 20 may be either permanent or reversible.

The web 10 may be made in a variety of manners. For instance, the layer 12 may be a three dimensional nonwoven web such as a high loft bonded carded web, a rush-transferred nonwoven web, a needle punched laminated web, a thermally molded fibrous web with bicomponent fibers, or any other type of web which may have elevated and depressed regions 14, 16. The functional material members 24 may then be affixed to the layer 12 at the cavities 18. The attachment of the functional material members 24 may be by any method, for instance adhesion may be used to attach the functional material members 24 to the layer 12.

In accordance with another exemplary embodiment of the present invention, the layer 12 may be an elastic nonwoven web such as a film or meltblown. The layer 12 may be stretched, and the functional material members 24 may be relatively rigid, and either printed or adhered to the layer 12. The layer 12 may be allowed to contract, allowing the layer 12 to pucker upwards around the functional material members 24. In accordance with one exemplary embodiment of the present invention, the layer 12 may include a shape memory polymer. In such an instance, the geometry of the layer 12 may change from one orientation to the next upon the heating or cooling of the layer 12.

An alternative way to construct the web 10 is found in placing the functional material members 24 onto a layer 12 that is substantially flat. The layer 12 may then be molded or held into a three dimensional shape with the functional material members 24 located a distance $D_1$ from the uppermost portion 26 of the layer 12. At this point, the reinforcing layer 32 may be bonded to the depressed regions 16 of the layer 12. As stated, the reinforcing layer 32 may be either elastic or inelastic.

An alternative method of making the web 10 exists in providing a relatively inelastic film or other nonwoven web which is then stretched. At this point, functional material members 24 are attached to the layer 12. The layer 12 may then be heated in order to cause the layer 12 to contract, resulting in puckered regions between the functional material members 24. A reinforcing layer 32 may be optionally attached to the layer 12 in order to form the web 10, as in the case of the web 10 shown in FIGS. 7 and 8.

The web 10 may be configured to be used as a cleaning tool, such as a dishwashing wipe. The web 10 may also be used as a cleaning surface on a scrubby pad, sponge, or sponge substitute. In such an instance, the web 10 may be used as an exfoliation tool in order to clean the user's skin.

The web 10 may also be configured such that the functional material members 24 are part of a fastening system. For instance, the functional material members 24 may be a tacky material adhesive 46, a pressure sensitive adhesive 46, a thermally activatable adhesive 46, a hook 40 and/or loop 48 of a hook and loop fastener system, and/or a gecko-like adhesive 46. The web 10 may be used in order to fasten diapers 56, incontinence briefs, disposable bibs, surgical gowns, disposable clothing of any kind, and/or disposable training pants for children. The web 10 may also be used as a replacement for adhesive tabs in feminine care products, or may be used in any other application in which an attachment system is needed.

Gecko-like adhesives are those that mimic the adhesive characteristics of gecko feet. Principles of gecko adhesion are discussed in more detail in Kelly Autumn et al., "Evidence for van der Waals Adhesion in Gecko Setae," *Proceedings of the National Academy of Sciences of the United States of America*, Vol. 99, No. 19, pp. 12,252-12,256 (Sep. 17, 2002); in Robert J. Full et al., "Adhesive Microstructure and Method of Forming the Same," WO 01/49776, published Jul. 12, 2001; in U.S. application Ser. No. 10/039,574, "Adhesive Microstructure and Method of Forming Same," filed Jan. 2, 2002 by K. Autumn and published as US20030124312-A1 on Jul. 3, 2003; and in U.S. application Ser. No. 10/197,763, "Adhesive Microstructure and Method of Forming Same," filed Jul. 17, 2002 by R. Fearing and published as US 20030208888-A1 on Nov. 13, 2003; all of which are incorporated by reference herein in their entireties. In general, gecko-like materials can have plurality of microscopic protrusions rising from a surface, the protrusions having a diameter of about 0.1 to 1 microns and a height of about 0.5 microns to about 500 microns, said protrusions being effective at adhering to an opposing surface without the use of pressure-sensitive adhesives.

The cross-sectional shape of the layer 12 may have various configurations in accordance with different exemplary embodiments of the present invention. For instance, the cross-sectional shape of the layer 12 shown in FIG. 2 is generally sinusoidal, while the cross-sectional shape of the layer 12 shown in FIG. 12 is in the form of alternating V-shapes.

Figure 18:
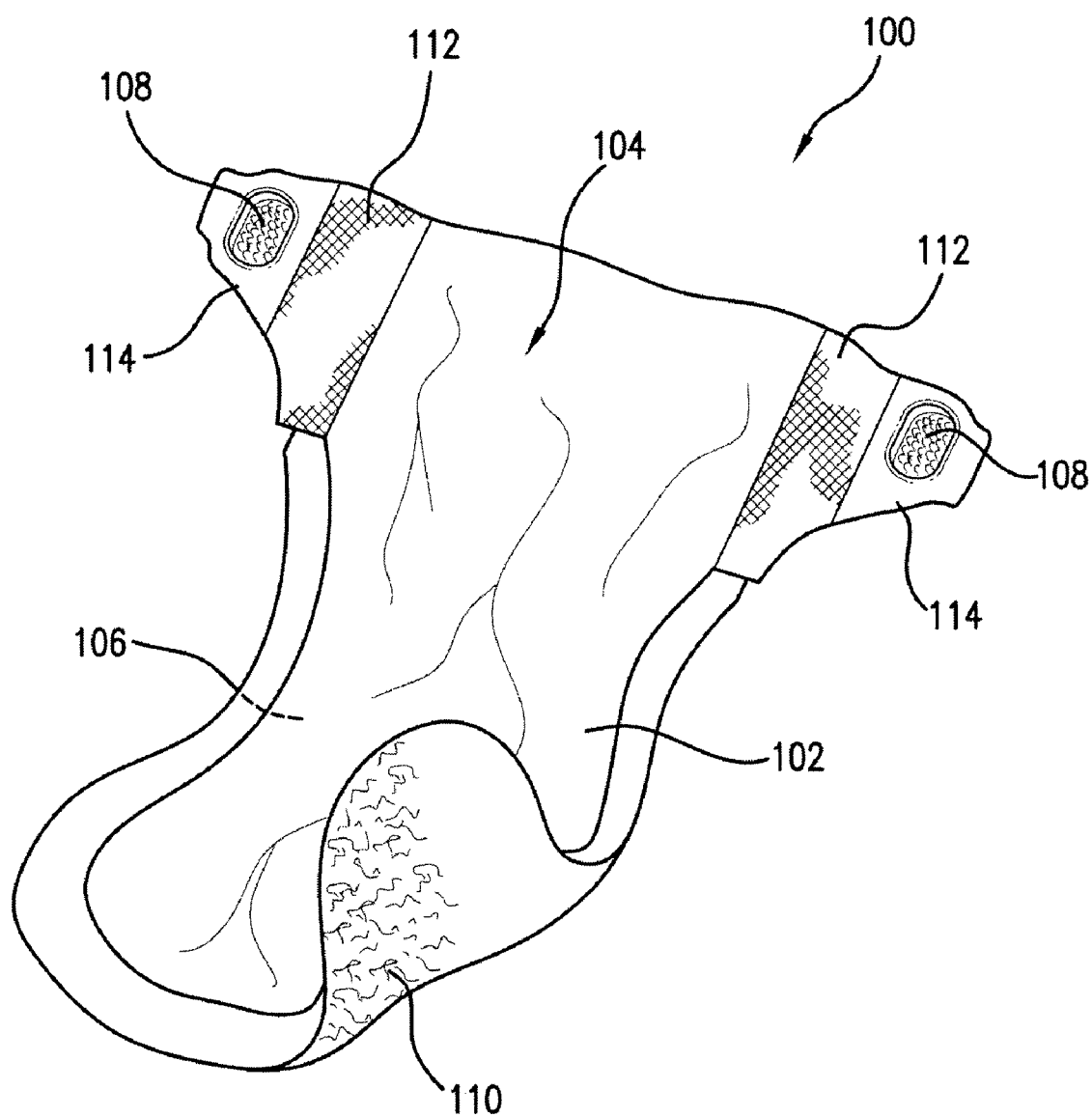
FIG. 18 is a perspective view of an article, which in this case is a diaper, that has a fastening member positioned in a recessed orientation below a surface of the body portion of the diaper.

The present invention also provides for an article 100 as shown in FIG. 18, which in this instance is a diaper. The article 100 has a body portion 102 with a first surface 104 and a second surface 106 disposed opposite therefrom. The body portion 102 may be made of any suitable material as is commonly known in the art, for instance an absorbent material may be included either attached to the body portion 102 or comprising the entire body portion 102. The body portion 102 has a pair of ears which include stretch members 112. The stretch members 112 may be neck bonded laminates. Neck bonded laminates are a composite material that has at least two layers in which one layer is a necked, non-elastic layer and the other layer is an elastic layer. The layers are joined together when the non-elastic layer is in an extended (necked) condition. Examples of neck-bonded laminates may be found in U.S. Pat. Nos. 5,226,992; 4,981,747; 4,965,122; and 5,336, 545, the contents of these four U.S. patents are incorporated by reference into the present application in their entirety for all purposes. Note that the ears are generally made of different materials than the remainder of the body portion 102.

Attached to the stretch members 112 are tab members 114. The tab members 114 may be a spunbond/meltblown/spunbond material in accordance with one exemplary embodiment of the present invention. The spunbond portion includes a plurality of small diameter fibers that are formed by extruding molten thermoplastic material as filaments from a plurality of fine, usually circular capillaries of a spinneret with the diameter of the extruded filaments then being rapidly reduced to fibers. Spunbond fibers incorporating the spunbond portion are generally continuous and have diameters that are generally greater than 7 microns, and more particularly between about 10 and about 20 microns. The meltblown portion of the tab member 114 includes meltblown fibers that are fibers that are formed by extruding a molten thermoplastic material through a plurality of fine, usually circular guide capillaries as molten threads or filaments into converging high velocity usually hot gas streams which attenuate the filaments of molten thermoplastic material to reduce their diameter. Afterwards, the meltblown fibers are carried by the high velocity gas stream and are deposited on a collecting surface to form a web of randomly dispersed meltblown fibers. Meltblown fibers are microfibers which may be continuous or discontinuous with diameters generally less than 10 microns.

The tab members 114 each include a fastening member 108. The fastening members 108 have a recessed orientation as shown in FIG. 18 in which the fastening members 108 are positioned below the first surface 104 of the body portion 102 (or below the first surface of the ear). The fastening members 108 are hooks of a hook and loop type fastener system. The counterpart loops 110 of the hook and look type fastener system are included on the second surface 106 of the body portion 102. Due to the fact that the fastening member 108 is recessed below the first surface 104, the fastening member 108 is protected from being place into engagement with the loops 110, hence preventing unwanted attachment of one portion of the article 100 to another portion of the article 100. Additionally, if several articles 100 are packaged together with one another, the fastening member 108 will be prevented from engaging and being attached to portions of different articles 100.

As such, the fastening member 108 is prevented from being prematurely engaged with another object. This configuration also allows the article 100 to remain in an open, unfolded position. It is sometimes the case that a person applying a diaper may need to unfold portions of the diaper that contain a fastening element and then position this fastening element to a location in which it is capable of properly securing the diaper. By having the fastening member 108 recessed, the article 100 may already be placed into an unfolded and extended condition, hence eliminating these series of steps by a person applying the article 100.

Figure 19:
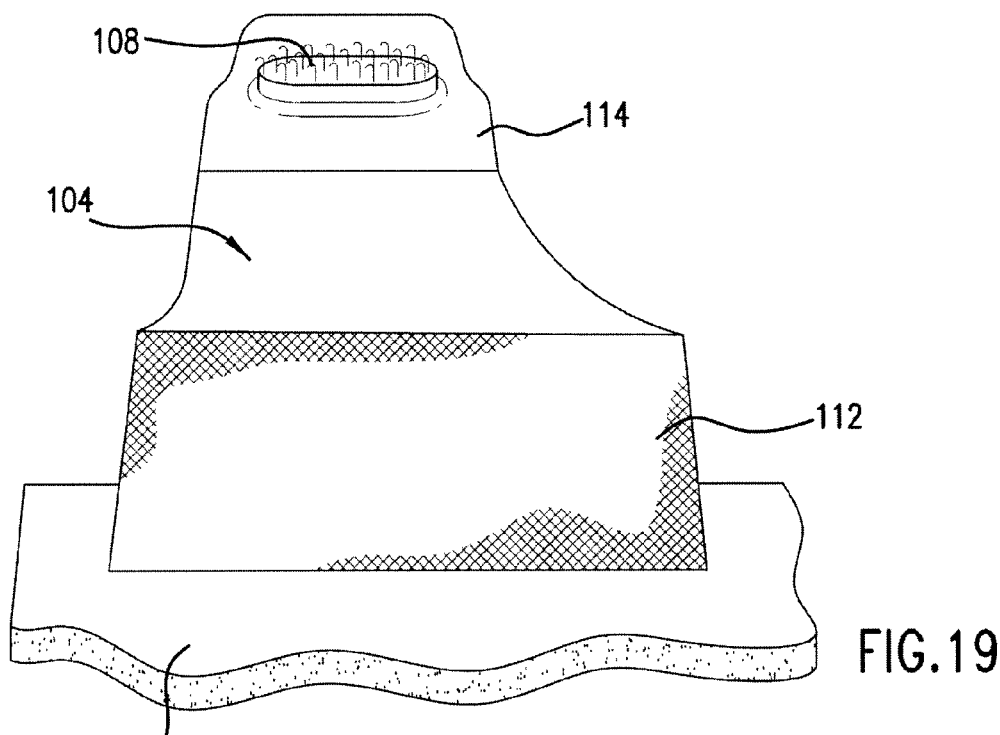
FIG. 19 is a perspective view of a portion of an article which has a fastening member positioned in an elevated orientation.
Figure 20:
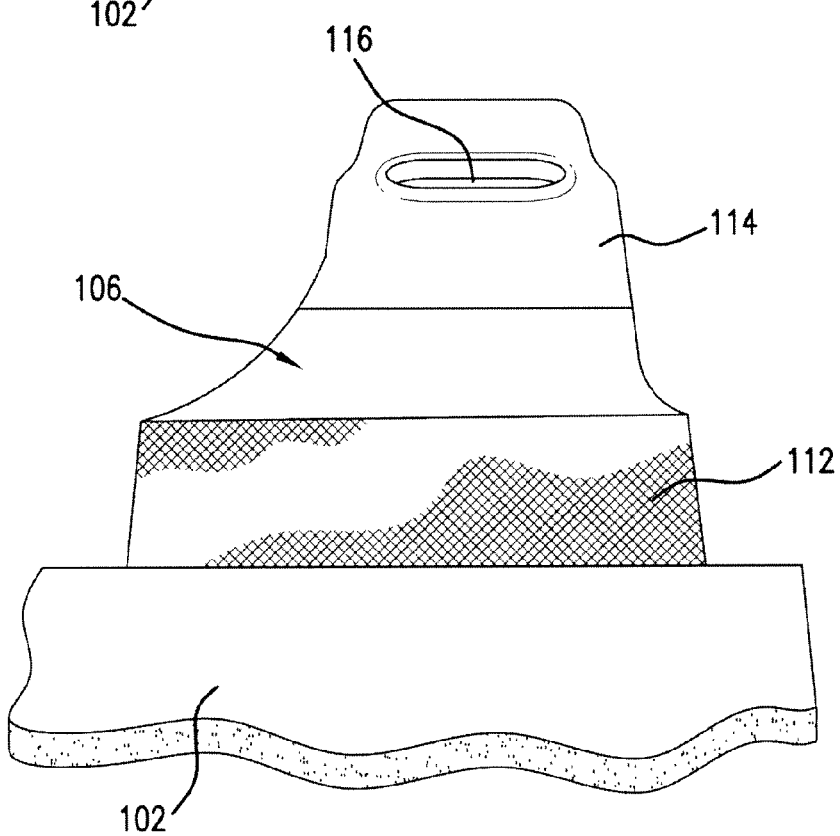
FIG. 20 is a perspective view of a portion of the article shown in FIG. 19 which shows the opposite side from that shown in FIG. 19.

The fastening member 108 may be moved from the recess orientation shown in FIG. 18 to an elevated orientation in which the fastening member 108 is available for engaging the loops 110. FIGS. 19 and 20 show the stretch member 112 and tab member 114 of the body portion 102. In FIG. 19, the first surface 104 of the body portion 102 is visible. The fastening member 108 is positioned into an elevated orientation in which the fastening member 108 is located above the first surface 104. As such, the fastening member 108 is no longer recessed below the first surface 104. The elevated orientation of the fastening member 108 allows for the hooks of the fastening member 108 to engage corresponding loops 110 (FIG. 18).

The fastening member 108 may have a stiff backing material that must be pressed with a predetermined force until it can snap into a changed position. The fastening member 108 in this case may be said to be bistable, that is it has two distinct geometric configurations in which it can be configured. The force required to change from one geometric configuration to the other may be at least about 50 grams of force (gf), about 100 gf, about 200 gf, or about 400 gf. However, it is to be understood than the fastening member 108 may require any desired amount of force to move it to or from the elevated orientation.

Like FIG. 19, FIG. 20 shows the stretch member 112 and tab member 114 of the body portion 102. Here however, the second surface 106 of the body portion 102 is visible. A location 116 is present on the tab member 114. A user may press the tab member 114 at location 116 in order to invert the fastening member 108 (FIG. 19) such that the fastening member 108 is repositioned from the recessed orientation to the elevated orientation. The location 116 is proximate to the fastening member 108, and may in fact be located exactly opposite from the fastening member 108 on the second surface 106. In certain exemplary embodiments of the present invention, the user may again reposition the fastening member 108 such that it is repositioned from the elevated orientation back into the recessed orientation. This may be accomplished, for instance, by directly pressing the fastening member 108.

Although described as being hooks of a hook and loop type fastener system, the fastening member 108 may be configured differently in accordance with other exemplary embodiments of the present invention. For instance, the fastening member 108 may be loops from a hook and loop type fastener system, an adhesive, a gecko-like fastener, or the like. Additionally, although described as being a diaper, the article 100 may be any type of disposable absorbent article, for instance the article 100 may be an adult incontinence brief or a sanitary napkin.

Figure 21:
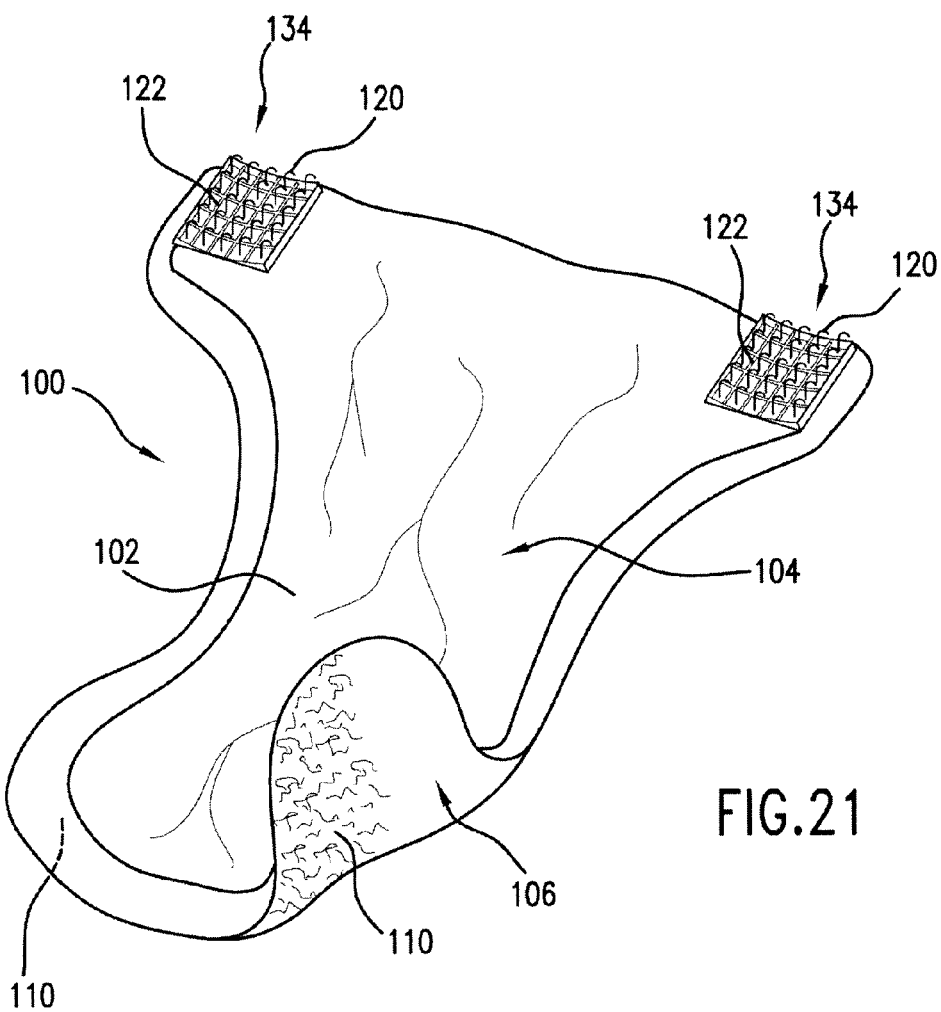
FIG. 21 is a perspective view of a diaper having an activatable fastening system disposed thereon in order to effect attachment of the diaper. The activatable fastening system is in the activated orientation.
Figure 22:
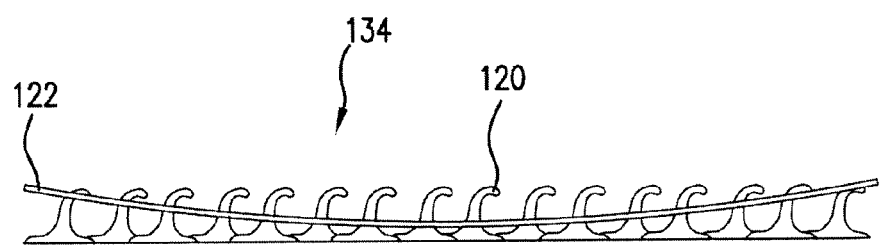
FIG. 22 is a side view of an activatable fastening system positioned in an activated orientation.

The present invention also provides for an alternative way of preventing premature engagement of a hook and loop type fastener. FIG. 21 shows an activatable fastening system 134 incorporated into an article 100 and used for attaching the article 100 onto a user. Again, in this instance the article 100 is a diaper, but it is to be understood that the activatable fastening system 134 may be employed on various types of articles 100. The activatable fastening system 134 includes a plurality of hooks 120 that may engage loops 110 and be retained thereon. As shown in FIG. 21, the hooks 120 are in an activated orientation in which the hooks 120 may engage the loops 110. This position is shown in FIG. 22, and it may be seen that the hooks 120 are curved and exposed such that the hooks 120 may engage the loops 110 (FIG. 21) and be retained thereon.

Figure 23:
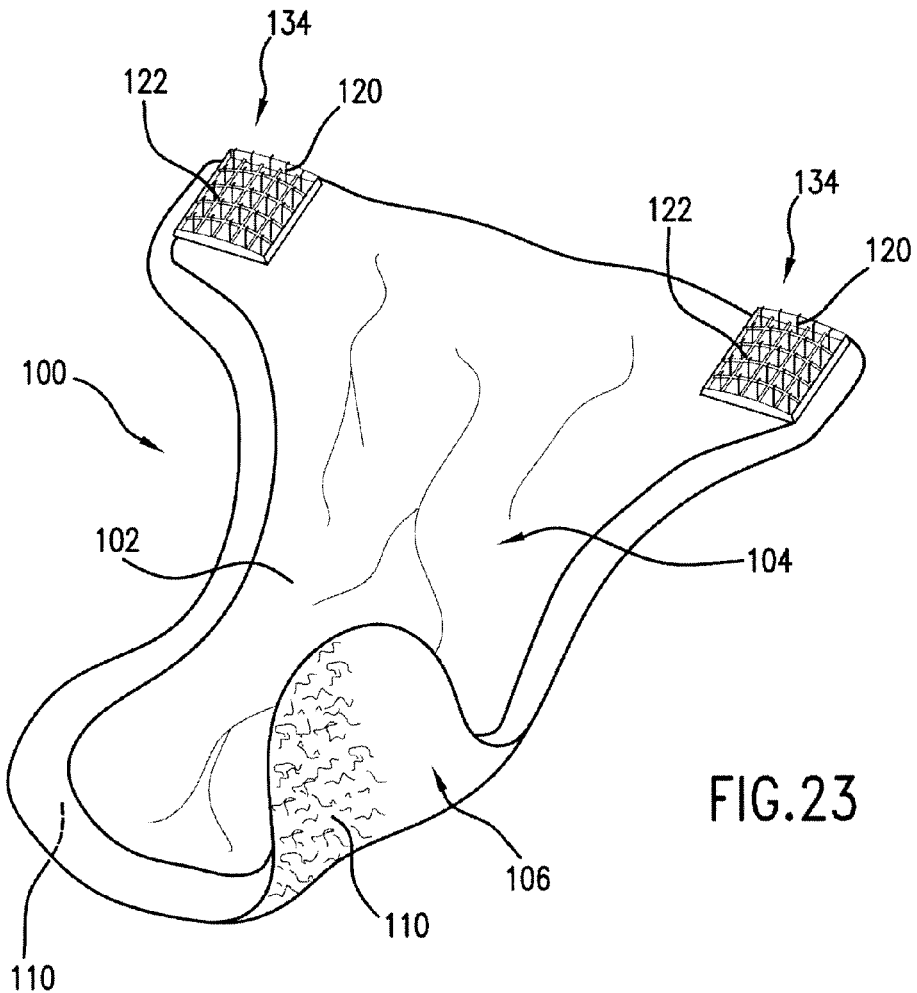
FIG. 23 is a perspective view of a diaper having an activatable fastening system used to effect attachment of the diaper. The activatable fastening system is positioned in a deactivated orientation.
Figure 24:
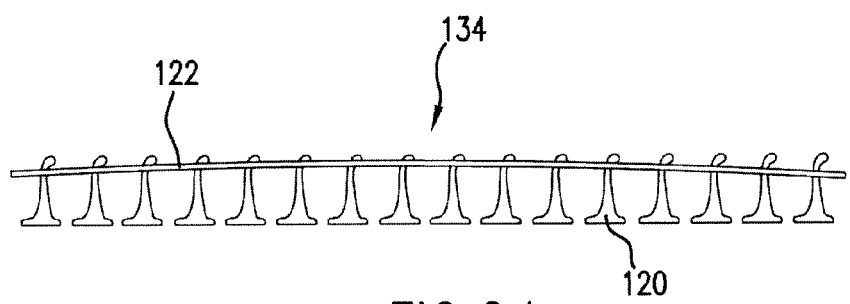
FIG. 24 is a side view of an activatable fastening system positioned in a deactivated orientation.

FIGS. 23 and 24 show the activatable fastening system 134 having hooks 120 that are positioned into a deactivated orientation. In this regard, an actuation member 122 that is included in the activatable fastening system 134 is activated by a user such that the actuation member 122 moves the hooks 120 into a deactivated orientation. In the deactivated orientation, the hooks 120 are less engageable with the loops 110 than when the hooks 120 are in the activated orientation. The hooks 120 are less engageable with the loops 110 when in the deactivated orientation because the actuation member 122 straightens out the hooks 120 such that the curvature of the hooks 120 is reduced. Reducing the curvature of the hooks 120 prevents the hooks 120 from engaging and being retained on the loops 110. Alternatively, the hooks 120 need not move, but may be shielded by motion of the actuation member 122 such that the hooks 120 are shielded from engaging contact with other materials. Thus, the actuation member 122 can serve as a shield that can be elevated or depressed relative to the level of the hooks 120 to respectively deactivate or activate the hooks 120.

As shown in the exemplary embodiments of FIGS. 21-24, the actuation member 122 is a wire frame. The hooks 120 extend through a plurality of openings 124 in the wire frame comprising the actuation member 122. The actuation member 122 is moveable by a user between the activated orientation and the deactivated orientation. The actuation member 122 may be initially biased in either the activated or deactivated orientation. The actuation member 122 may be made of a resilient material such that the actuation member 122 will remain in either the activated or deactivated orientation until a user presses the actuation member 122 into the opposite orientation. At such time, the actuation member 122 will then remain in this subsequent orientation until once again activated by the user. The actuation member 122 may store an amount of potential energy when in the activated or deactivated orientation, urging the actuation member 122 to move into the other orientation. A user may release this potential energy at a desired time, causing the actuation member 122 to move into its opposite orientation. The potential energy could be provided by inherent elastic properties of the material making up the actuation member 122. The potential energy could also be provided by the addition of filaments or malleable metal to the actuation member 122.

The actuation member 122 may be attached to a portion of the first surface 104 of the body portion 102. Although shown as being a wire frame, the actuation member 122 may be configured differently in accordance with other exemplary embodiments. For instance, the actuation member 122 may be a plastic resilient member that is essentially planer across with a plurality of holes distributed therethrough through which the hooks 120 are disposed. Further, the actuation member 120 may be configured as a generally planer object having a plurality of slits defined thereon through which the hooks 120 are disposed.

In the exemplary embodiment shown in FIGS. 21-24, the actuation member 122 applies a force perpendicular to the first surface 104 of the body portion 102. This force acts to straighten the hooks 120 such that the hooks 120 lose their ability to engage the loops 110.

Although the actuation member 122 may be pushed in order to reposition the hooks 120 between the activated and deactivated orientations, the actuation member 122 may also be "stretched" in order to effect the desired change in orientations. In this regard, a force may be applied in a direction parallel to the first surface 104 of the body portion 102. This force will act to stretch or to straighten the actuation member 122 such that it elongates or moves into a position in which the hooks 120 may be moved into a different orientation. Also, the actuation member 122 may be "compressed" such that the actuation member 122 is again repositioned and consequently causes a repositioning of the hooks 120.

Figure 32:
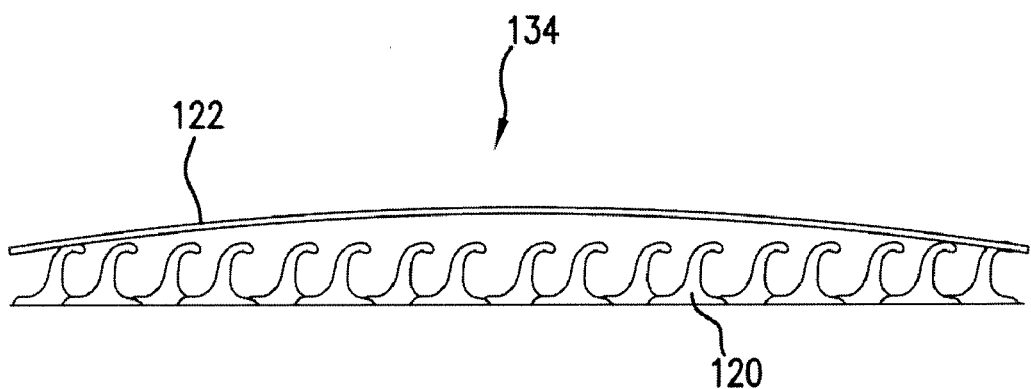
FIG. 32 is a side view of an activatable fastening system shown in a deactivated orientation.

The activatable fastening system 134 of the present invention may also be configured such that the hooks 120 are not physically reoriented. In this regard, the hooks 120 may remain in the same shape in both the activated orientation and in the deactivated orientation. Here, the actuation member 122 acts as a shield to the hooks 120 when in the deactivated orientation. For instance, the actuation member 122 may be a wire frame that is disposed on the outer surface of the hooks 120 and lie at the base of the hooks 120 when in the activated orientation. When moved into the deactivated orientation, the actuation member 122 is moved upwards such that the actuation member 122 is placed over at least a portion of the curvature of the hooks 120. In such an instance, the actuation member 122 will act as a shield to prevent the hooks 120 from engaging the loops 110. The actuation member 122 may be moved entirely above the top of the hooks 120, or may alternatively be moved to approximately the midpoint of the height of the hook 120. In this manner, the actuation member 122 may be configured to completely prevent engagement of the hooks 120 with the loops 110, or may be configured to prevent a certain degree of engagement between the hooks 120 and the loops 110. FIG. 32 (described later) shows an embodiment where the actuation member 122 shields the hooks 120.

The activatable fastening system 134 may be provided with any type of actuation member 122 known to those skilled in the art. For instance, the actuation member 122 may be configured such that it stores an amount of potential energy when activated by the user. In this case, the activatable fastening system 134 may be provided in the deactivated orientation to the user, and then activated by the user and moved into the activated orientation. This movement causes the actuation member 122 to store an amount of potential energy. This potential energy could be provided by elastic properties of the actuation member 122. The stored potential energy may be released by the user such that the actuation member 122 is moved, causing the hooks 120 to be moved into the deactivated orientation.

Figure 25:
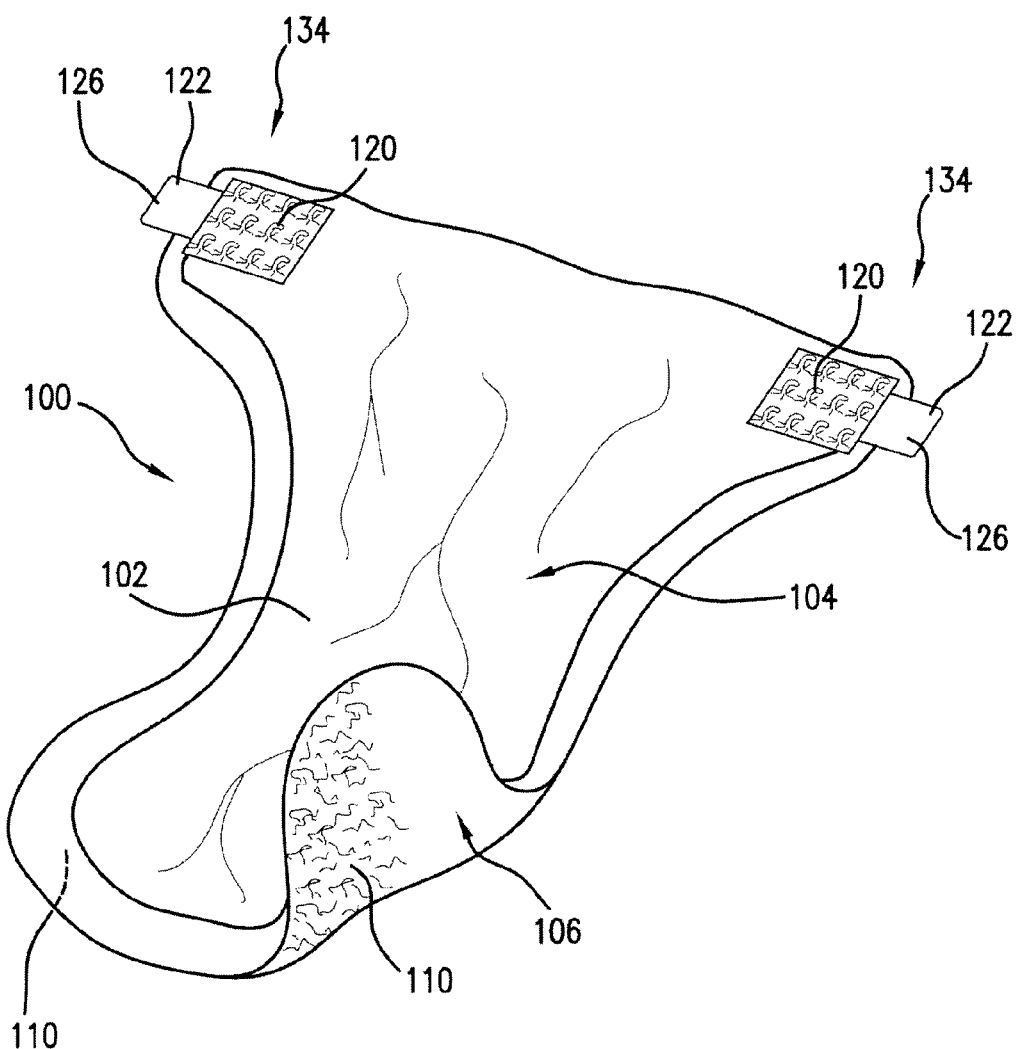
FIG. 25 is a perspective view of a diaper having an activatable fastening system that includes a rigid portion disposed in hollow interiors of a plurality of hooks. The activatable fastening system is shown in the activated orientation.
Figure 26:
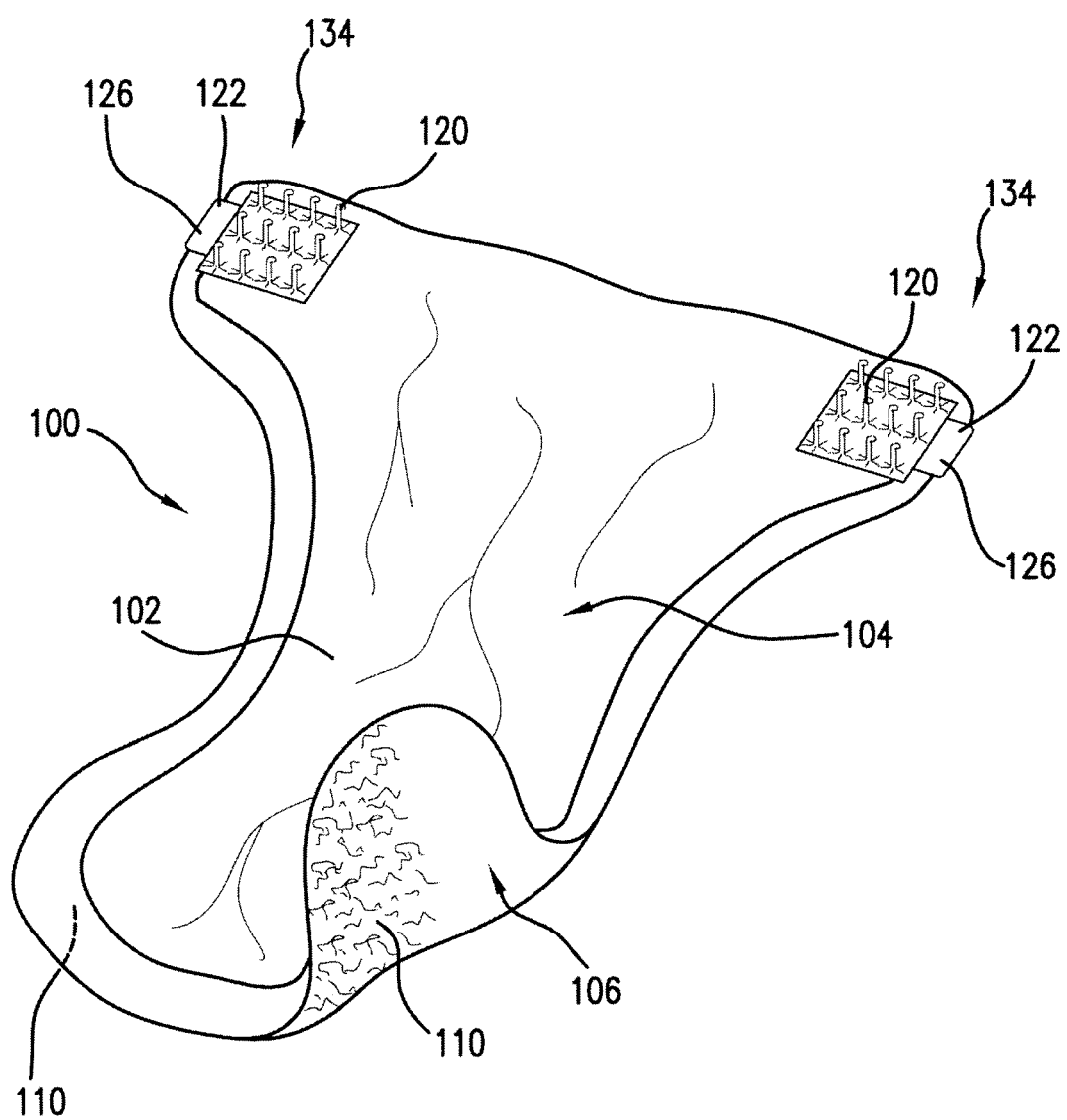
FIG. 26 is a perspective view of a diaper having the activatable fastening system shown in FIG. 25. Here, the activatable fastening system is shown in the deactivated orientation.
Figure 27:
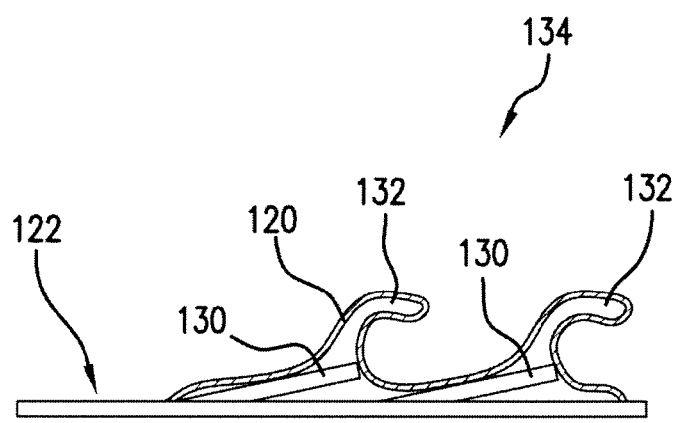
FIG. 27 is a cross-sectional view of an activatable fastening system having a rigid portion disposed in hollow interiors of hooks. The activatable fastening system is in the activated orientation.
Figure 28:
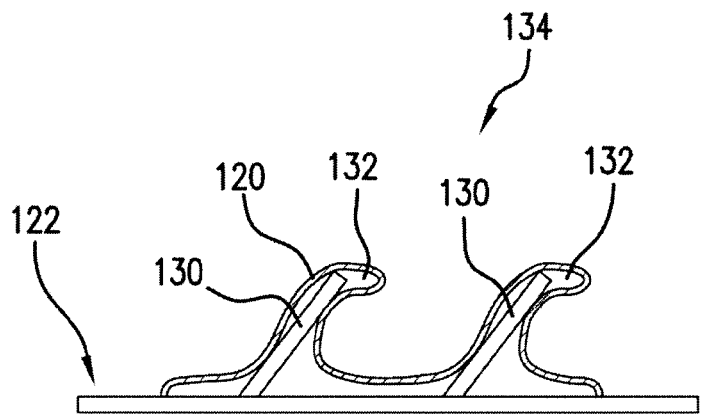
FIG. 28 is a cross-sectional view of the activatable fastening system of FIG. 27. The activatable fastening system is shown in a semi-activated orientation.
Figure 29:
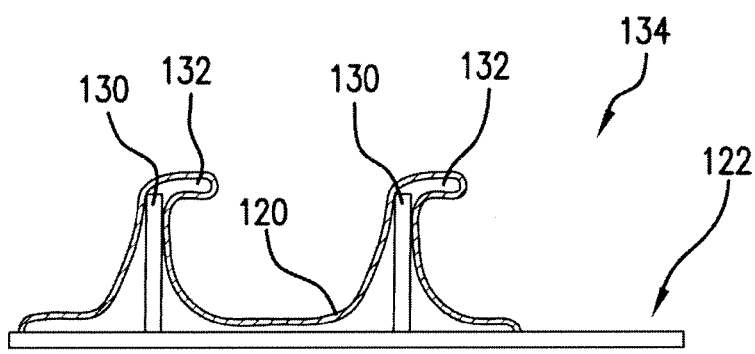
FIG. 29 is a cross-sectional view of the activatable fastening system shown in FIG. 27. The activatable fastening system is shown in the deactivated orientation.

An alternative exemplary embodiment of the activatable fastening system 134 is shown in FIGS. 25-29. The activatable fastening system 134 is again shown in FIG. 25 as being incorporated into an article 100 that is a diaper. The hooks 120 of the activatable fastening system 134 are shown in the activated orientation in which they may engage and be retained on the loops 110. Referring now to FIGS. 27-29, the hooks 120 each define a hollow interior 132. The actuation member 122 has a plurality of rigid portions 130 that are disposed in the hollow interiors 132 of the hooks 120. FIG. 27 shows the positioning of the actuation member 122 and the rigid portions 130 of the hooks 120 in the activated orientation. The actuation member 122 may be moved laterally as shown in FIGS. 27-29 such that the rigid portions 130 are pivoted upwards. Movement of the rigid portions 130 necessarily causes the hooks 120 to likewise be moved. This movement results in a straightening of the hooks 120 and a reducing of the curvature of the hooks 120, reducing their effectiveness in being retained on the loops 110 as previously discussed.

FIG. 27 shows the hooks 120 in the activated orientation while FIG. 28 shows the hooks 120 in a semi-activated orientation. Here, the hooks 120 are still capable of engaging the loops 110, but are less engageable with the loops 110 than when in the activated orientation in FIG. 27. FIG. 29 shows the hooks 120 in the deactivated orientation in which the hooks 120 are even less engageable with the loops 110 than when in the semi-activated orientation.

The actuation member 122 may be moved back and forth such that the hooks 120 are repeatably positionable between the activated, semi-activated, and deactivated orientations.

FIG. 25 shows the actuation member 122 having a tab 126 that may be grasped by a user. FIG. 26 shows the tab 126 being moved such that the actuation member 122 is subsequently moved and causes the hooks 120 to be moved into the deactivated orientation. It is to be understood that the present invention is not limited to the use of a tab 126 in order to cause movement of the actuation member 122. In accordance with other exemplary embodiments of the present invention, the actuation member 122 may be moved in any manner commonly known to those skilled in the art.

Figure 30:
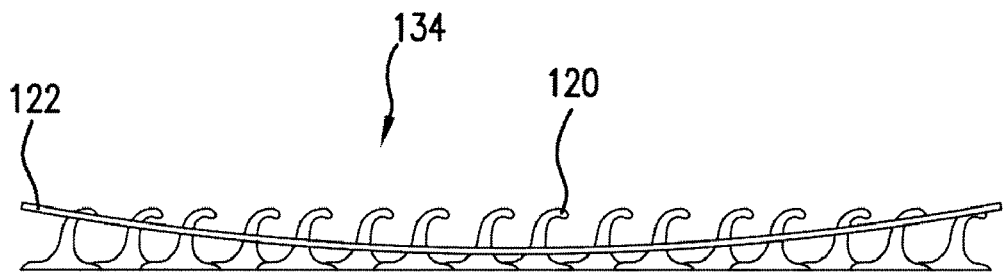
FIG. 30 is a side view of an activatable fastening system shown in an activated orientation.
Figure 31:
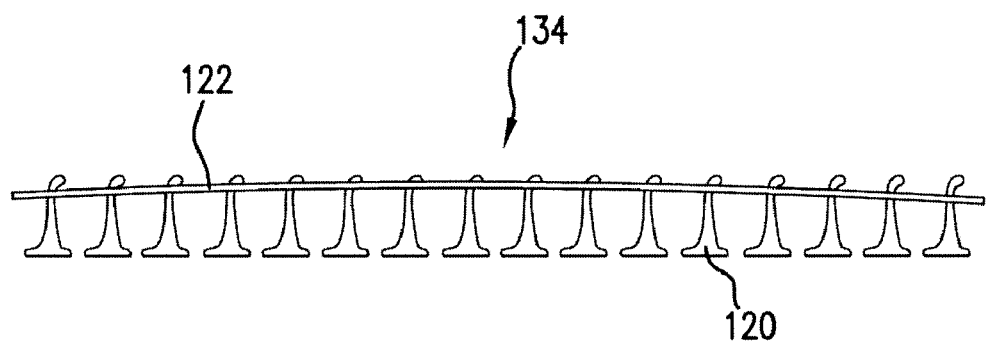
FIG. 31 is a side view of an activatable fastening system shown in a semi-activated orientation.

FIGS. 30-32 show an alternative exemplary embodiment of the activatable fastening system 134 in accordance with the present invention. FIG. 30 shows the activatable fastening system 134 in an activated orientation in which the hooks 120 may engage the loops 110 and be retained thereon. The actuation member 122 may be pulled in the lateral direction, or may be pushed by a user such that the actuation member 122 is repositioned as that shown in FIG. 31. Here, the hooks 120 are moved in response to movement of the actuation member 122 into a semi-activated orientation. In this instance, the hooks 120 are less capable of engaging the loops 110 than when in the activated orientation of FIG. 30. FIG. 32 shows the actuation member 122 being moved such that the actuation member 122 is above the hooks 120 and constitutes a deactivated orientation of the activatable fastening system 134. The actuation member 122 thus shields the hooks 120 and prevents them from engaging the loops 110. Movement between the orientations shown in FIGS. 30-32 may be reversible in certain exemplary embodiments, or may be irreversible in accordance with other exemplary embodiments.

In accordance with one exemplary embodiment of the present invention in which the article 100 is a diaper, the actuation member 122 may have a "button" printed thereon which conveys the purpose and location of the actuation member 122 to the user. In this instance, the user may press the "button", hence moving the actuation member 122 and activating the activated fastening system 134. The "buttons" could be printed on either the actuation member 122 itself, or onto another portion of the body portion 102.

It is to be understood that the activatable fastening system 134 is not limited to an article 100 that is a diaper. For instance, the activatable fastening system 134 may be incorporated into other products such as feminine care pads, adult incontinence pads, shoes, cable straps, removable surface mountings, and any other application which may employ a hook and loop type fastener.

It should be understood that the present invention includes various modifications that can be made to the embodiments of the web 10 and activatable fastening system 134 as described herein as come within the scope of the appended claims and their equivalents.

EXAMPLE 1

Figure 33:
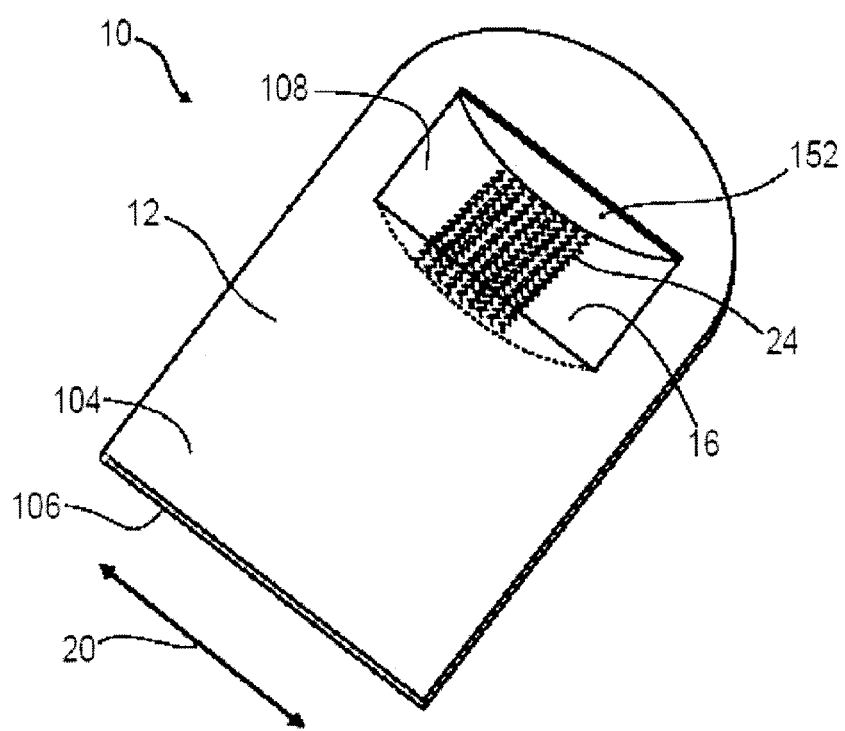
FIG. 33 is a perspective view of an activatable fastening system shown in the deactivated orientation having functional members that occupy only the central portion of the fastening member.

Rapid prototyping was used to create a substantially rigid web having an internal flexing member (a fastening member) with functional elements thereon. The rapid prototyping was done using a DTM Sintestation 2500 Plus manufactured by 3D Systems (Valencia, Calif.). Duraform material was used to create the solid part, which was generated by the device based on a CAD drawing of an embodiment web according the present invention. FIG. 33 depicts a web 10, substantially similar to the web manufactured by rapid prototyping. The web 10 comprises a substantially flat, rigid layer 12 having an upper first surface 104 and a lower second surface 106. The layer 12 also comprises a fastening member 108 in a central portion of the layer 12. The fastening member 108 also comprises upward extending functional members 24 such as hook elements for engaging an object facing the first surface 104 of the layer 12.

The fastening member 108 can flex between two orientations. Portions of the rigid layer 12 surround the fastening member 108 and prevent it from extending in the longitudinal direction 20, though its arc length in the longitudinal direction is greater than the straight in-plane width of the fastening member 108, such that it could extend longitudinally were it not for the restraint imposed by the rigid material of the layer 12. As shown the fastening member 108 is in a downward, inactive orientation, buckled away from the first surface of the layer 12 with the fastening members 24 disposed below the first surface 104 of the layer 12. A vertical gap 152 exists between the sides of the fastening member 108 and the plane of the layer 12. After the fastening member 108 is flexed upward into an elevated orientation (not shown), similar vertical gap 152 may be established due to the height difference between the fastening member 108 and the plane of the layer 12.

The fastening member 108 in the duraform-based web 10 made by rapid prototyping had a thickness of about 20 mils. The actual web differed from the web 10 of FIG. 33 in the functional elements (hooks) extended completely across the curved surface of the fastening member 108, whereas in FIG. 33 the functional members only occupy the central portion of the fastening member.

The manufactured article had dimensions generally suitable for use as an ear in a diaper or incontinence brief. It allowed the fastening member 108 to buckle between two orientations, a downward, inactive orientation and an upward, activated orientation in which the hooks (functional members 24) were disposed away from the layer in an engageable relationship for attachment to loop material.

What is claimed is:

1. An activatable fastening system, comprising:
    a plurality of hooks from a hook and loop fastener, the hooks having an activated orientation in which the hooks are engageable with loops from a hook and loop fastener in order to be retained thereon, and wherein the hooks have a deactivated orientation in which the hooks are less engageable with the loops from a hook and loop fastener than when in the activated orientation;
    an actuation member engageable with the plurality of hooks and activatable by a user such that the actuation member moves laterally;
    a plurality of rigid portions fixed to the actuation member; and
    wherein a rigid portion is disposed within each hook such that when the actuation member moves laterally, the rigid portions pivot and reposition the plurality of hooks between the activated orientation and the deactivated orientation.

2. The activatable fastening system as set forth in claim 1, wherein in the deactivated orientation the actuation member reduces the amount of curvature of the hooks.

3. The activatable fastening system as set forth in claim 1, wherein the actuation member is biased into a position such that the actuation member positions the hooks in the deactivated orientation.

4. The activatable fastening system as set forth in claim 1, wherein:
    the hooks define a hollow interior;
    the rigid portion is entirely disposed in the hollow interior of the hooks, actuation of the actuation member reduces the amount of curvature of the hooks when the hooks are repositioned from the activated orientation to the deactivated orientation.

5. The activatable fastening system as set forth in claim 1, wherein the actuation member is pushed by a user in order to reposition the hooks from the activated orientation to the deactivated orientation.

6. The activatable fastening system as set forth in claim 1, wherein in the deactivated orientation the hooks are completely prevented from engaging the loops and being retained thereon.

7. The activatable fastening system as set forth in claim 1, wherein the hooks have a semi-activated orientation in which the hooks are less engageable with the loops than in the activated orientation but are more engageable with the loops than in the deactivated orientation, the actuation member repositions the hooks between the activated, semi-activated, and deactivated orientations.

8. The activatable fastening system as set forth in claim 1, wherein the rigid portions form a substantially acute angle with the actuation member when the hooks are in the activated orientation.

9. The activatable fastening system as set forth in claim 1, wherein the rigid portions form a substantially 90° angle with the actuation member when the hooks are in the deactivated orientation.

10. The activatable fastening system as set forth in claim 1, wherein movement of the rigid portions define an arc when repositioning the hooks between the activated and deactivated orientations.

* * * * *